(12) United States Patent
Sand et al.

(10) Patent No.: US 7,972,340 B2
(45) Date of Patent: *Jul. 5, 2011

(54) SYSTEMS AND METHODS FOR INJECTING FLOWABLE MATERIALS INTO BONES

(75) Inventors: Paul M. Sand, San Carlos, CA (US);
Mark A. Reiley, Piedmont, CA (US);
Arie Scholten, Manteca, CA (US);
Robert M. Scribner, Niwot, CO (US);
Michael L. Reo, Redwood City, CA (US)

(73) Assignee: Kyphon SARL, Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/718,415

(22) Filed: Mar. 5, 2010

(65) Prior Publication Data
US 2010/0160923 A1 Jun. 24, 2010

Related U.S. Application Data

(60) Continuation of application No. 11/528,160, filed on Sep. 27, 2006, now Pat. No. 7,704,256, which is a division of application No. 10/630,519, filed on Jul. 30, 2003, now Pat. No. 7,731,720, which is a division of application No. 09/893,298, filed on Jun. 27, 2001, now Pat. No. 6,645,213, which is a continuation-in-part of application No. 09/496,987, filed on Feb. 2, 2000, now Pat. No. 6,719,761, which is a division of application No. 08/910,809, filed on Aug. 13, 1997, now Pat. No. 6,048,346.

(60) Provisional application No. 60/214,666, filed on Jun. 27, 2000.

(51) Int. Cl.
*A61B 17/58* (2006.01)
(52) U.S. Cl. .............................. 606/92; 606/93; 606/94
(58) Field of Classification Search .............. 606/91–94, 606/191–194; 604/272, 508, 60; 433/224; 222/386.5, 399
See application file for complete search history.

(56) References Cited

U.S. PATENT DOCUMENTS

| 3,926,705 | A | 12/1975 | Todd |
| 4,338,925 | A | 7/1982 | Miller |
| 4,551,135 | A | 11/1985 | Gorman et al. |
| 4,627,434 | A | 12/1986 | Murray |
| 4,653,487 | A | 3/1987 | Maale |

(Continued)

FOREIGN PATENT DOCUMENTS

DE 3443167 A1 6/1986

(Continued)

OTHER PUBLICATIONS

Osteo-Site Bone Access Products, Cook Inc., 2002.

(Continued)

*Primary Examiner* — Pedro Philogene
(74) *Attorney, Agent, or Firm* — Haynes and Boone, LLP

(57) ABSTRACT

A cavity creation device is introduced into a cancellous bone volume of a vertebral body through a percutaneous access path. The cavity creating device is manipulated to form a cavity in the cancellous bone volume. A volume of filling material is placed in the cavity by introducing a tube through the percutaneous access path and by conveying the filling material through a side dispensing port of the tube.

7 Claims, 15 Drawing Sheets

U.S. PATENT DOCUMENTS

| | | | |
|---|---|---|---|
| 4,969,888 A | | 11/1990 | Scholten et al. |
| 4,976,688 A | | 12/1990 | Rosenblum |
| 5,108,404 A | * | 4/1992 | Scholten et al. ............... 606/94 |
| 5,112,305 A | | 5/1992 | Barath et al. |
| 5,219,897 A | | 6/1993 | Murray |
| 5,231,989 A | * | 8/1993 | Middleman et al. ........... 600/434 |
| 5,300,048 A | | 4/1994 | Drewes, Jr. et al. |
| 5,324,273 A | | 6/1994 | Discko, Jr. |
| 5,342,325 A | | 8/1994 | Lun et al. |
| 5,380,276 A | | 1/1995 | Miller et al. |
| 5,397,304 A | | 3/1995 | Truckai |
| 5,468,245 A | | 11/1995 | Vargas, III |
| 5,545,136 A | | 8/1996 | Berger |
| 5,562,619 A | | 10/1996 | Mirarchi et al. |
| 5,569,196 A | | 10/1996 | Muni et al. |
| 5,571,189 A | | 11/1996 | Kuslich |
| 5,681,317 A | | 10/1997 | Caldarise |
| 5,704,909 A | | 1/1998 | Morrey et al. |
| 5,728,066 A | | 3/1998 | Daneshvar |
| 5,755,797 A | | 5/1998 | Baumgartner |
| 5,800,409 A | | 9/1998 | Bruce |
| 5,817,057 A | | 10/1998 | Berenstein et al. |
| 5,849,014 A | | 12/1998 | Mastrorio et al. |
| 5,972,015 A | | 10/1999 | Scribner et al. |
| 5,980,504 A | | 11/1999 | Sharkey et al. |
| 6,010,449 A | | 1/2000 | Selmon et al. |
| 6,019,765 A | | 2/2000 | Thornhill et al. |
| 6,048,346 A | | 4/2000 | Reiley et al. |
| 6,086,594 A | | 7/2000 | Brown |
| 6,113,576 A | | 9/2000 | Dance et al. |
| 6,348,055 B1 | | 2/2002 | Preissman |
| 6,383,190 B1 | | 5/2002 | Preissman |
| 6,395,007 B1 | | 5/2002 | Bhatnagar et al. |
| 6,412,667 B1 | | 7/2002 | Huang |
| 6,506,214 B1 | * | 1/2003 | Gross ........................ 623/19.11 |
| 6,547,432 B2 | | 4/2003 | Coffeen et al. |
| 6,582,446 B1 | | 6/2003 | Marchosky |
| 6,592,559 B1 | | 7/2003 | Pakter et al. |
| 6,599,293 B2 | | 7/2003 | Tague et al. |
| 6,706,069 B2 | | 3/2004 | Berger |
| 6,719,761 B1 | | 4/2004 | Reiley et al. |
| 6,852,095 B1 | | 2/2005 | Ray |
| 6,979,341 B2 | | 12/2005 | Scribner et al. |
| 7,704,256 B2 | * | 4/2010 | Sand et al. ...................... 606/92 |
| 7,713,273 B2 | | 5/2010 | Krueger et al. |

FOREIGN PATENT DOCUMENTS

| | | |
|---|---|---|
| EP | 0747114 B1 | 12/1996 |
| GB | 2338428 A | 12/1999 |

OTHER PUBLICATIONS

Bone cement delivery engineered to your procedural needs, Ava-Tex Bone Cement Delivery System, CardinalHealth, 2003.

SpinalSpecialties, Inc., 2003.

SpinalSpecialties, Inc., Precise injection from outside the fluoro field, Osteoject Bone Cement Delivery System, Sep. 2002.

Interpore Cross International, Biologic & Structural Innovation, The CDO System, 2001.

Office Action mailed Mar. 20, 2006 in U.S. Appl. No. 10/630,519, filed Jul. 30, 2003.

Office Action mailed Oct. 5, 2007 in U.S. Appl. No. 10/630,519, filed Jul. 30, 2003.

Office Action mailed Jan. 17, 2008 in U.S. Appl. No. 10/630,519, filed Jul. 30, 2003.

Office Action mailed Aug. 27, 2008 in U.S. Appl. No. 10/630,519, filed Jul. 30, 2003.

Office Action mailed Feb. 3, 2009 in U.S. Appl. No. 10/630,519, filed Jul. 30, 2003.

Office Action mailed Mar. 17, 2008 in U.S. Application Serial No. 10/528,160, filed Sep. 27, 2006.

* cited by examiner

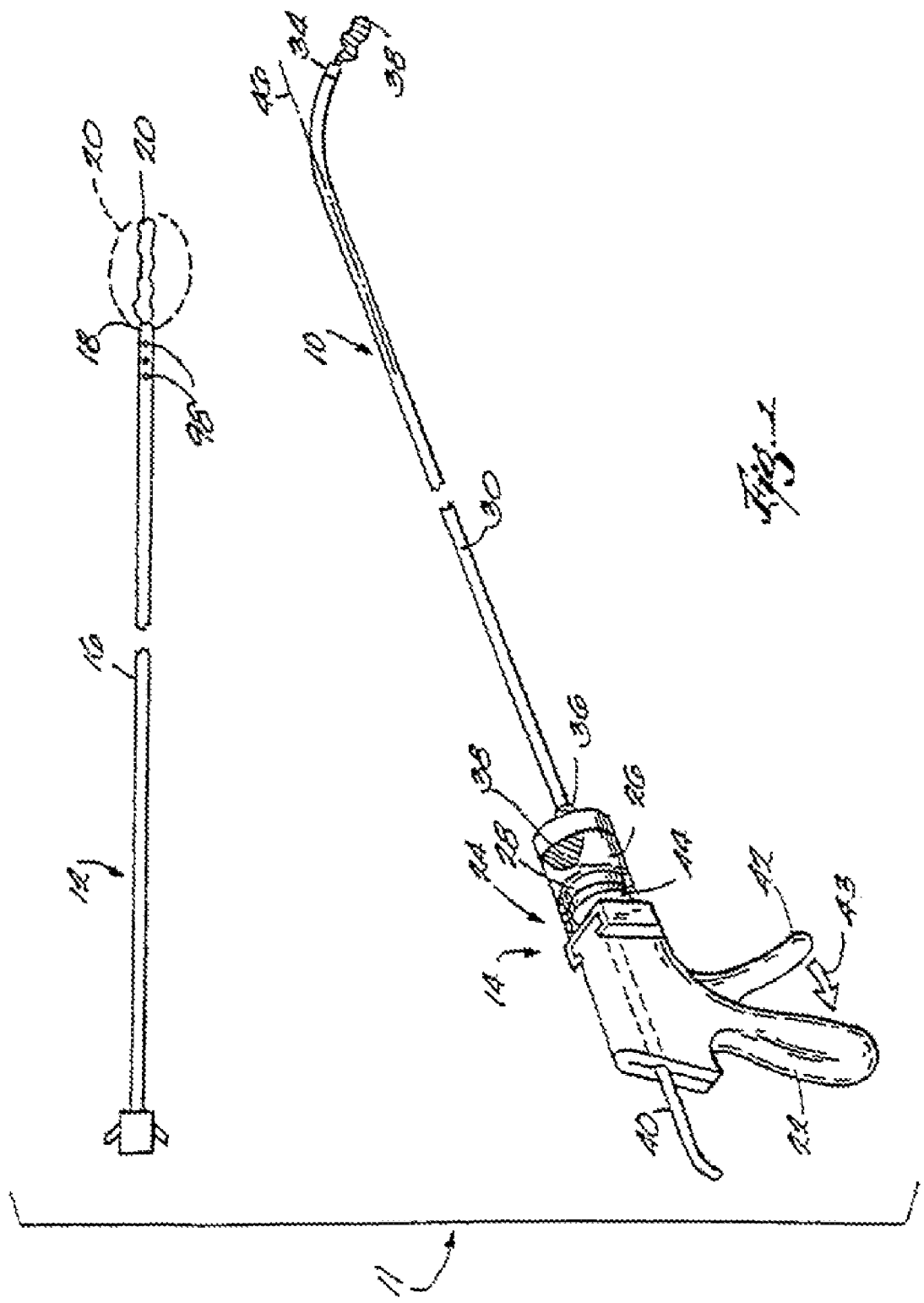

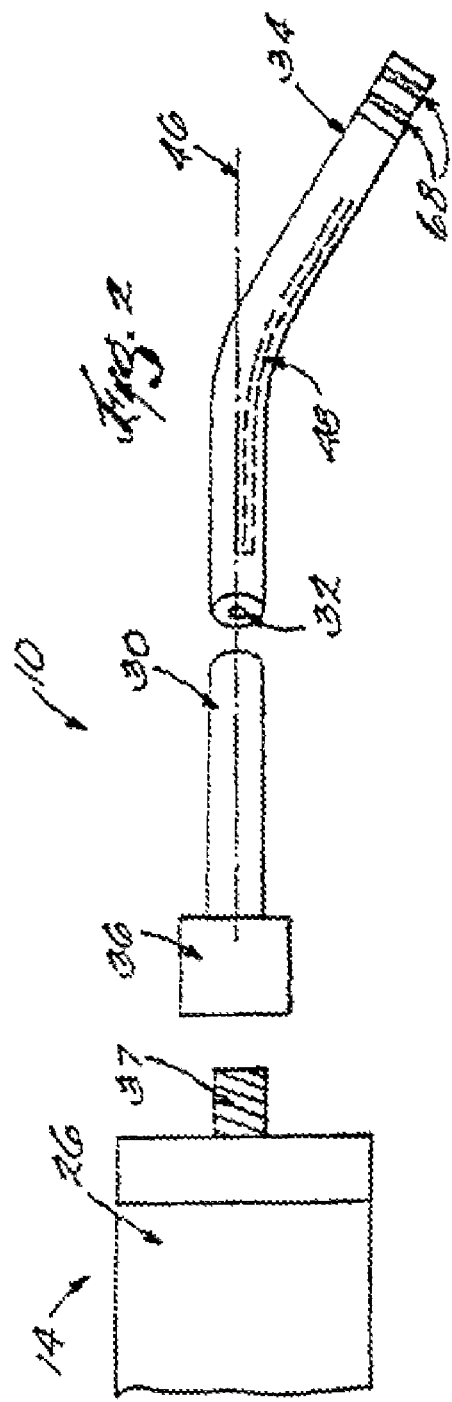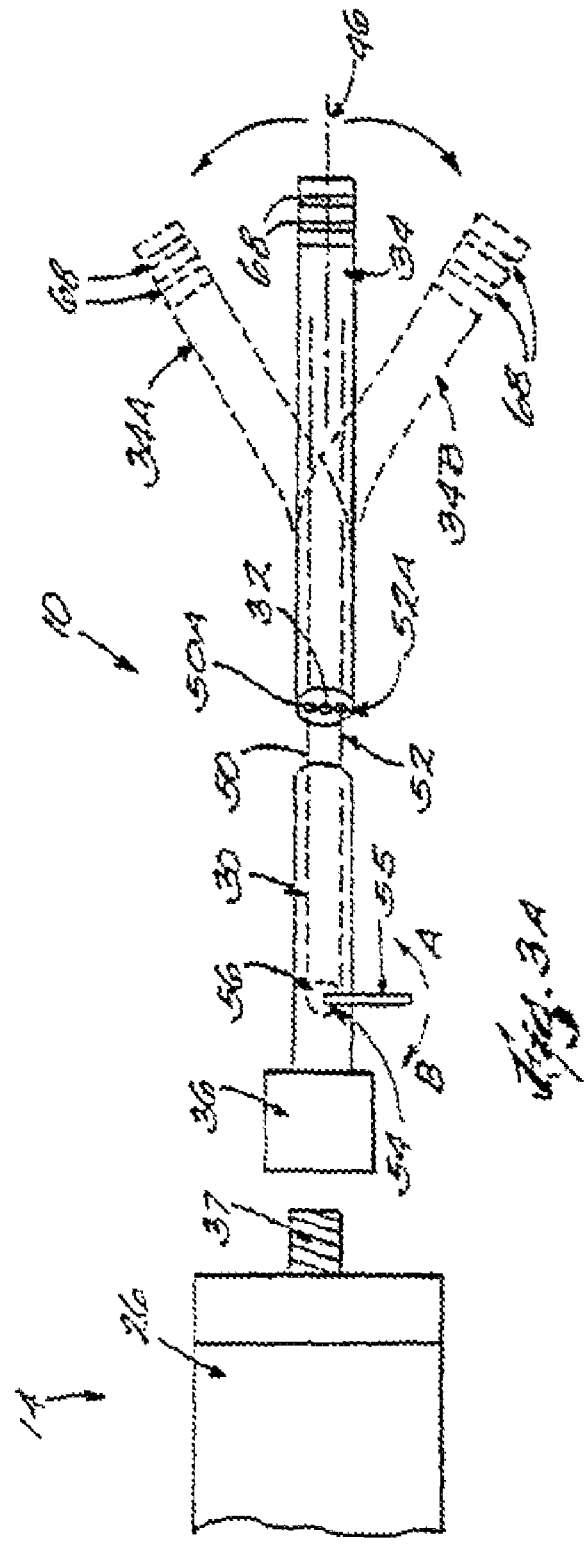

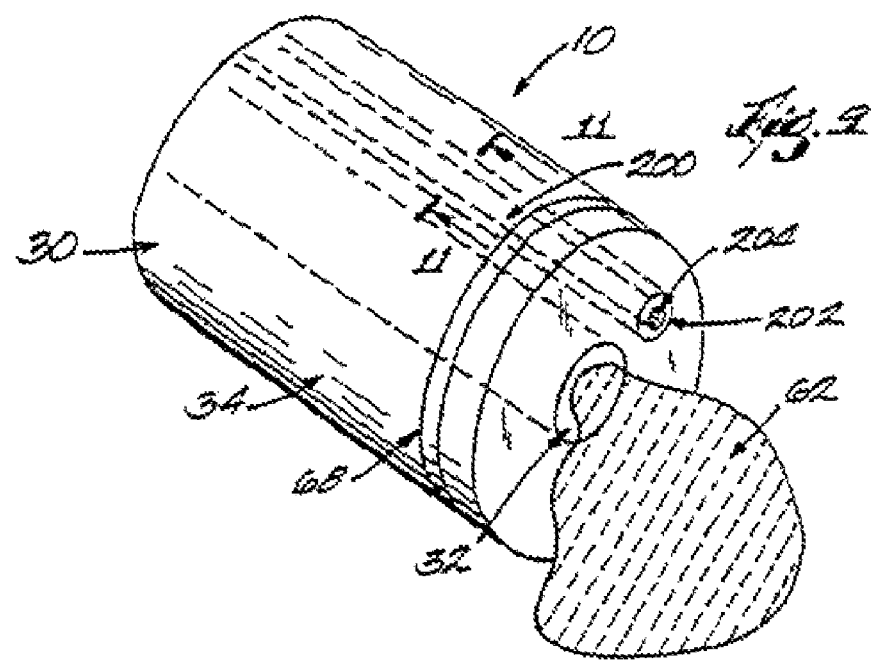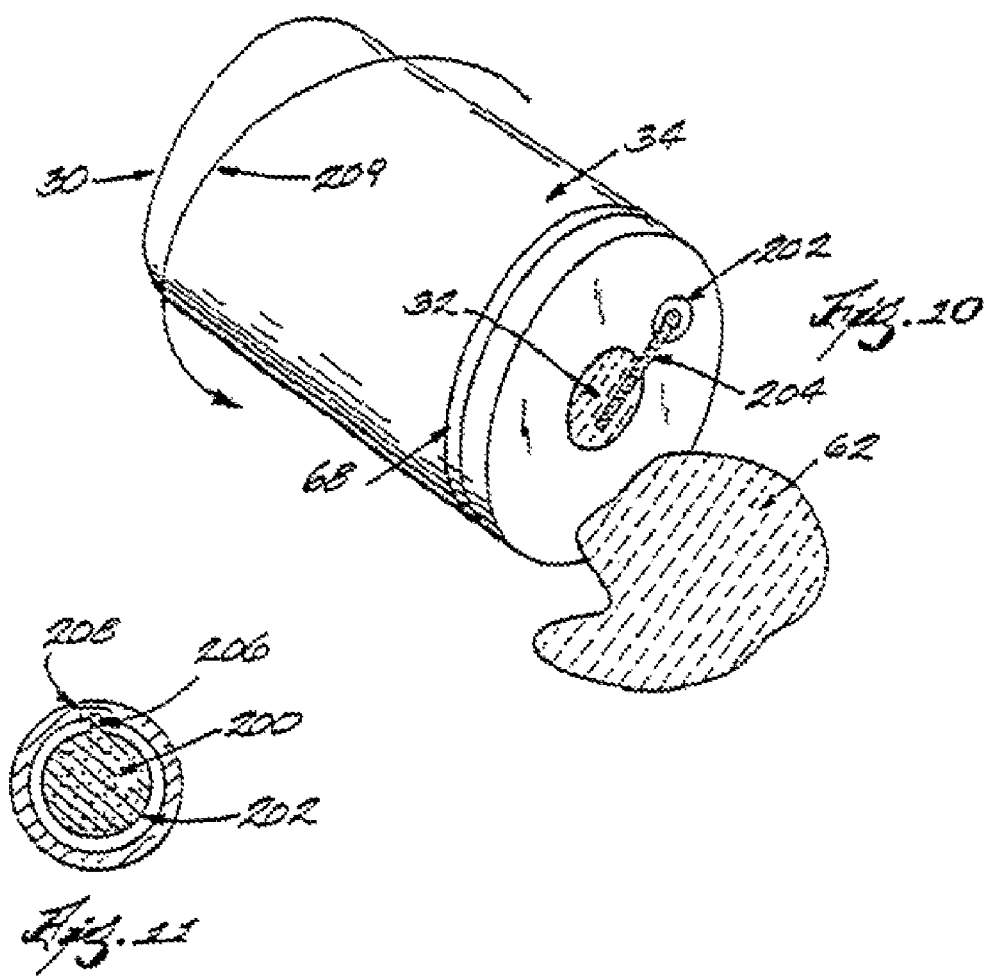

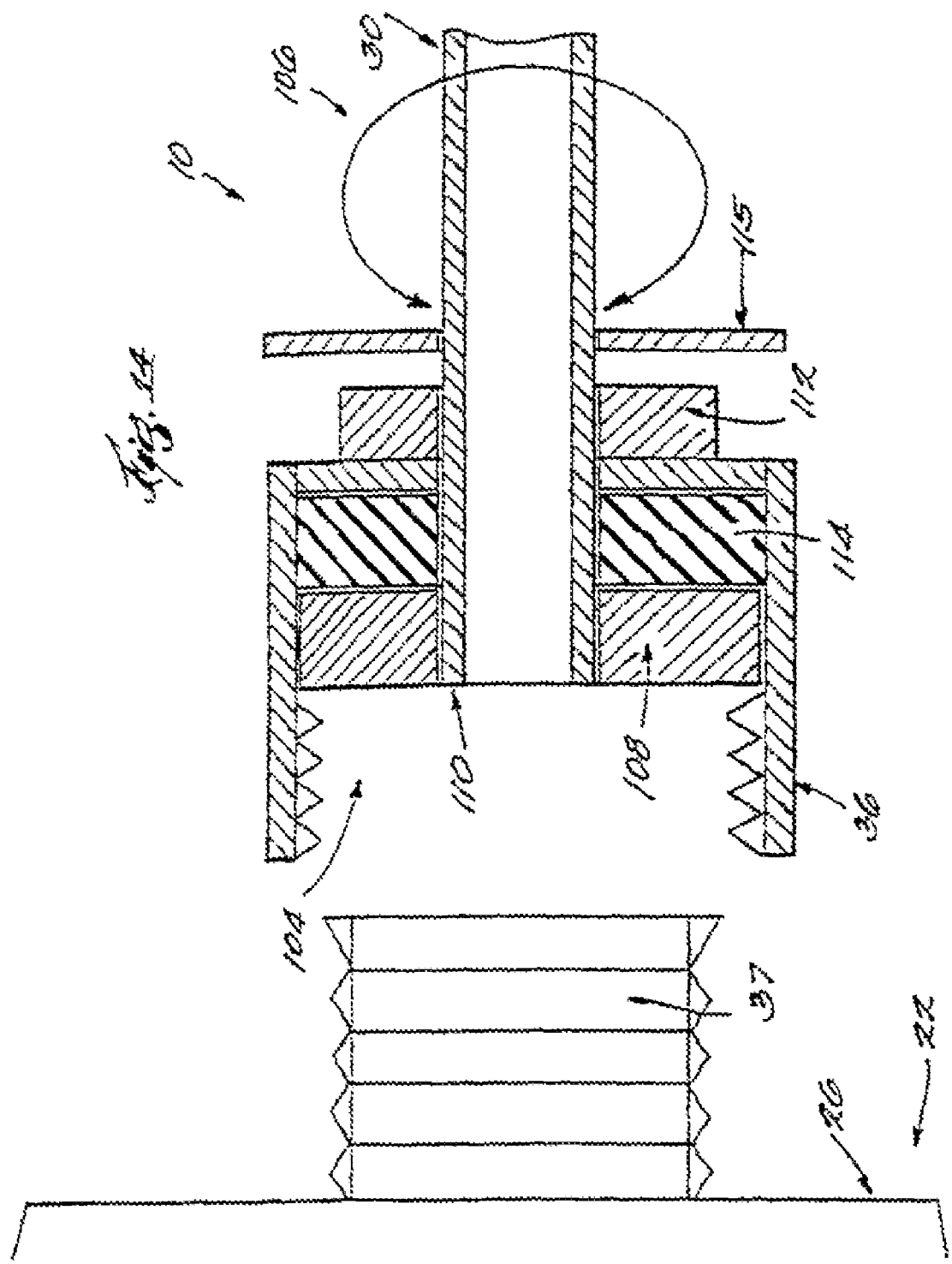

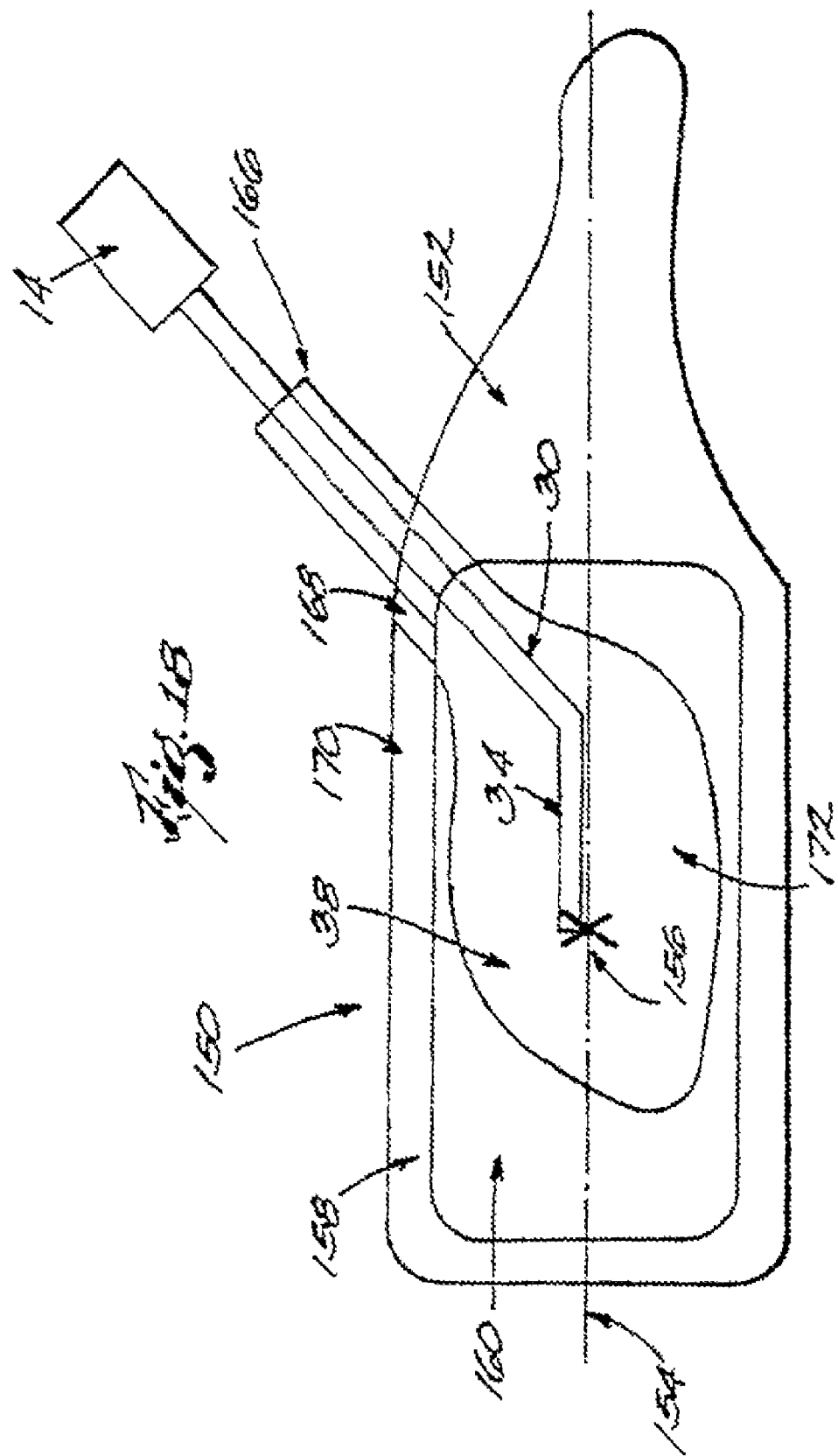

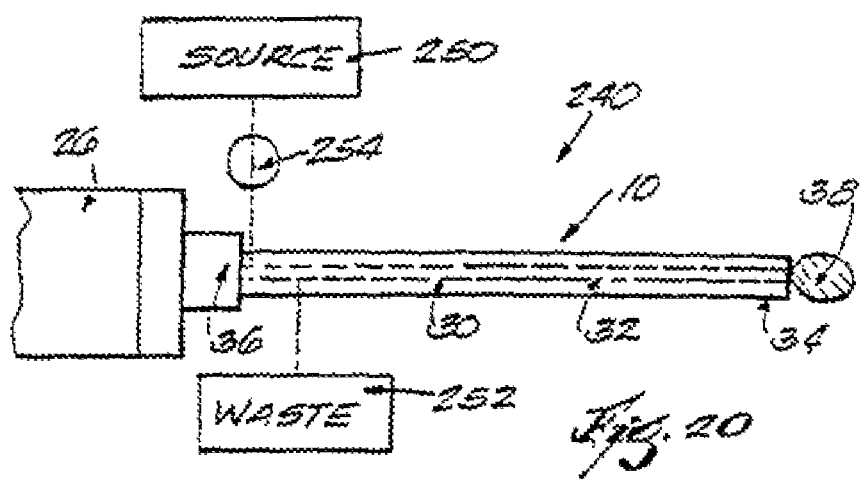
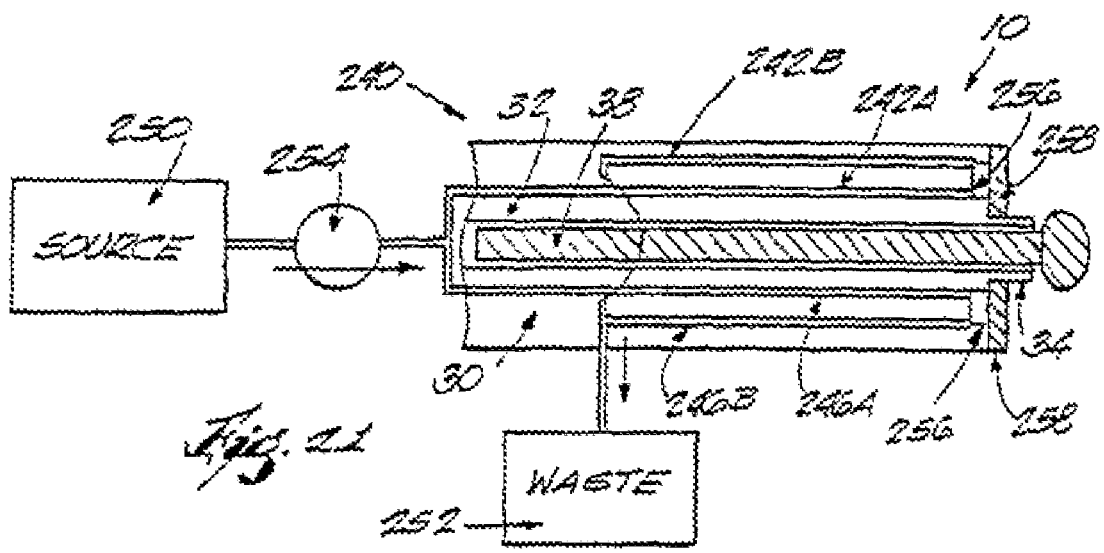
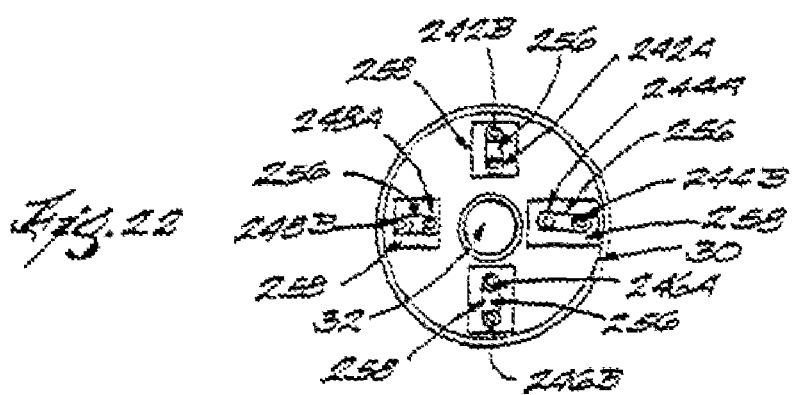

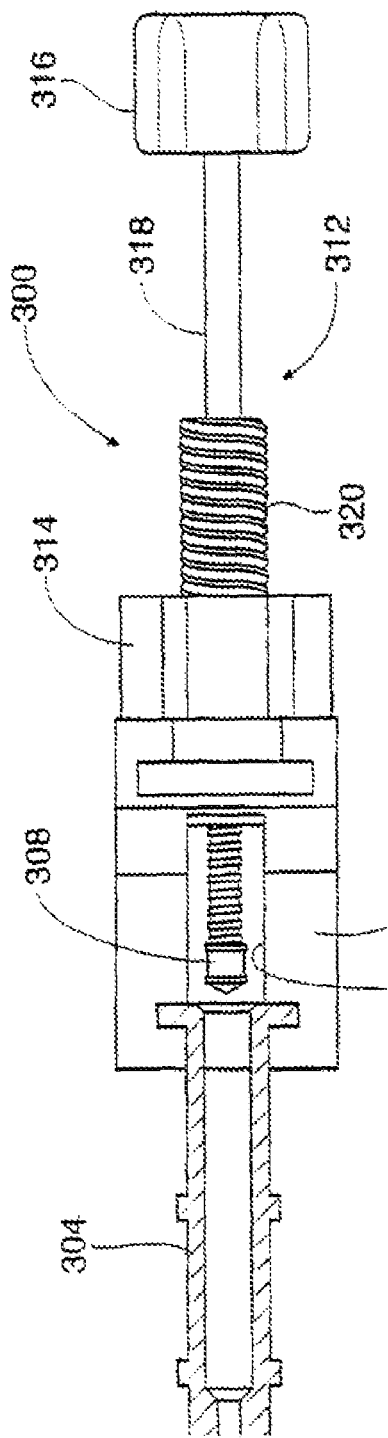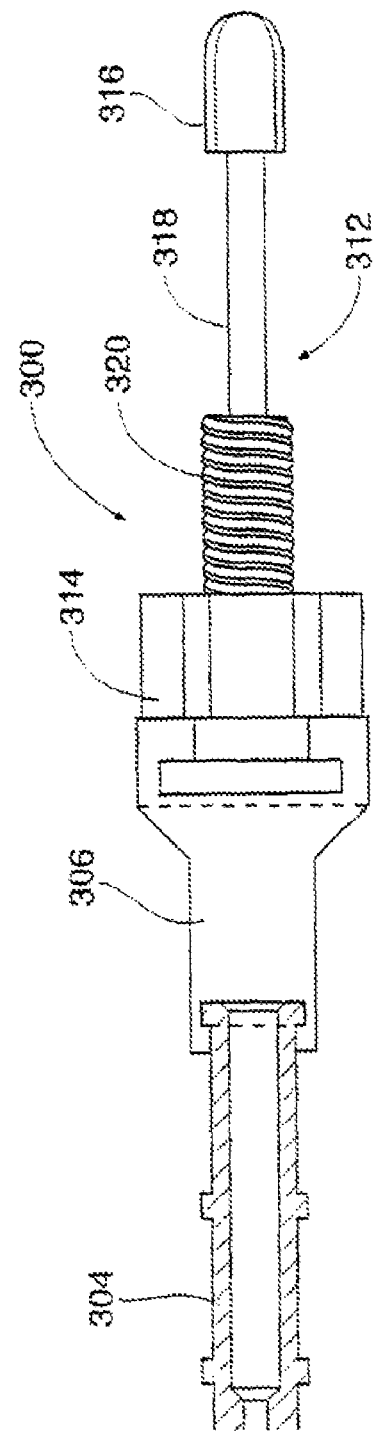

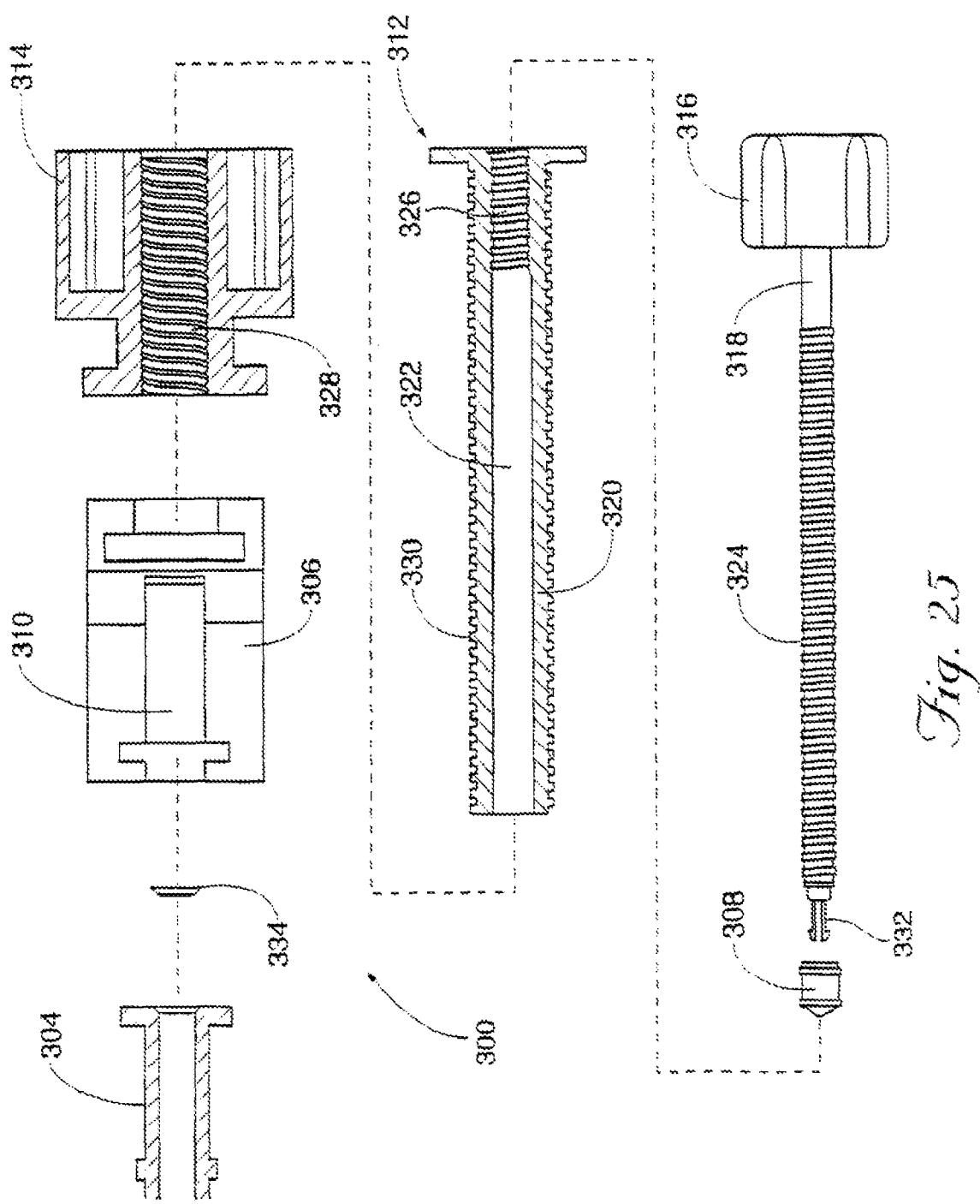

US 7,972,340 B2

SYSTEMS AND METHODS FOR INJECTING FLOWABLE MATERIALS INTO BONES

RELATED APPLICATION

This application is a continuation of co-pending U.S. patent application Ser. No. 11/528,160, filed Sep. 27, 2006, and entitled "Systems and Methods for Injecting Flowable Materials into Bones" which is a divisional of co-pending U.S. patent application Ser. No. 10/630,519, filed Jul. 30, 2003, and entitled "Systems and Methods for Injecting Flowable Materials Into Bone," which is a divisional of U.S. patent application Ser. No. 09/893,298, filed Jun. 27, 2001 (now U.S. Pat. No. 6,645,213), which claims the benefit of provisional application Ser. No. 60/214,666 filed 27 Jun. 2000, and which is also a continuation-in-part of U.S. patent application Ser. No. 09/496,987, filed Feb. 2, 2000 (now U.S. Pat. No. 6,719,761), which is a divisional of U.S. patent application Ser. No. 08/910,809, filed Aug. 13, 1997 (now U.S. Pat. No. 6,048,346), each of which is incorporated herein by reference.

FIELD OF THE INVENTION

The invention relates to the treatment of bone conditions in humans and other animals.

BACKGROUND OF THE INVENTION

Several companies offer mechanical bone cement injection devices. These devices are similar to a household caulking gun. Typically, the injection device has a pistol-shaped body, which supports a cartridge containing bone cement. The cement is typically in two-parts and must be mixed in a mixer and transferred into the cartridge for injection.

Just after mixing, and prior to curing, the cement is in a flowing, viscous liquid state, similar to a syrup or watery pancake batter in consistency. The injection device has a ram, which is actuated by a manually movable trigger or screwing mechanism for pushing the viscous bone cement out the front of the cartridge through a suitable nozzle and into the interior of a bone targeted for treatment.

Once injected into the targeted bone, the cement undergoes a curing cycle of perhaps 6 to 8 minutes. While curing, the cement passes from a viscous liquid to a putty-like consistency and finally to a hard rigid block.

SUMMARY OF THE INVENTION

The invention provides, in its various aspects, greater control over the placement of cement and other flowable liquids into bone.

One aspect of the invention provides systems and methods for introducing a filling material into a the cancellous bone volume of a vertebral body. The systems and methods introduce a cavity creation device into the vertebral body through a percutaneous access path, and manipulate the cavity creating device to form a cavity in the cancellous bone volume. The systems and methods place a volume of filling material in the cavity through the percutaneous access path by providing a tube for conveying the filling material through the percutaneous access path. The tube has a distal end region sized and configured for placement within the cavity. The distal end region includes a sidewall and a side dispensing port in the sidewall. The volume of filling material is placed in the cavity by conveyance through the side dispensing port.

Features and advantages of the inventions are set forth in the following Description and Drawings, as well as in the appended claims.

BRIEF DESCRIPTION OF THE DRAWINGS

FIG. 1 is a view of a system for treating bone, which includes a injector nozzle assembly embodying features of the invention;

FIG. 2 is an enlarged side view of the dispensing end of one embodiment of the injector nozzle assembly shown in FIG. 1, in which the dispensing end is prebent in a desired geometry to facilitate its deployment;

FIG. 3A is an enlarged side view of the dispensing end of another embodiment of the injector nozzle assembly shown in FIG. 1, in which the dispensing end is steerable to facilitate its deployment within bone;

FIG. 7 is an enlarged end view of the dispensing end of one embodiment of the injector nozzle assembly shown in FIG. 1, in which the dispensing end is steerable and also carries a loop formed for cutting cement free from the dispensing end;

FIG. 8 is an enlarged end view of the dispensing end of another embodiment of the injector nozzle assembly shown in FIG. 1, in which the dispensing end is steerable and also carries two loops formed for cutting cement free from the dispensing end;

FIG. 9 is an enlarged end view of the dispensing end of one embodiment of the injector nozzle assembly shown in FIG. 1, which carries a prebent stylet, which is shown in a retracted and straightened condition prior to use;

FIG. 10 is an enlarged end view of the dispensing end shown in FIG. 9, illustrating the rotation of the prebent stylet after advancement to cut free an ejected cement bolus;

FIG. 11 is a section view of the prebent stylet taken generally along line 11-11 in FIG. 9, showing a mating tab and keyway that prevents rotation of the stylet out of a desired orientation during use;

FIG. 12 is a side view of one embodiment of the injector nozzle assembly shown in FIG. 1, which includes a side port for dispensing cement;

FIG. 14 is an enlarged side section view of an injector nozzle assembly which includes a rotating fitting that allows the injector tube to be rotated independent of the cement injecting tool;

FIG. 15 is a side view of an injector nozzle assembly with a rotating fitting like that shown in FIG. 14, which includes index markers for ascertaining the orientation of the dispensing end and the extent to which the dispensing end is rotated, without need of direct visualization;

FIG. 18 is a lateral view of a vertebral body, partially cut away and in section, illustrating the deployment of the injector nozzle assembly shown in FIG. 1 by transpedicular access into a cavity previously formed by an expanded body;

FIG. 20 is a side view of a system which includes an injector nozzle assembly coupled to a source of cooling fluid to mediate the increase in temperature of curing cement dispensed by the assembly;

FIG. 21 is a somewhat diagrammatic side section view of the injector nozzle assembly shown in FIG. 20;

FIG. 23 is a side view, with portions broken away and in section, of an alternative injector nozzle assembly providing variable rates of delivery;

FIG. 24 is a top view, with portions broken away and in section, of the injector nozzle assembly shown in FIG. 23;

Figure 3B:
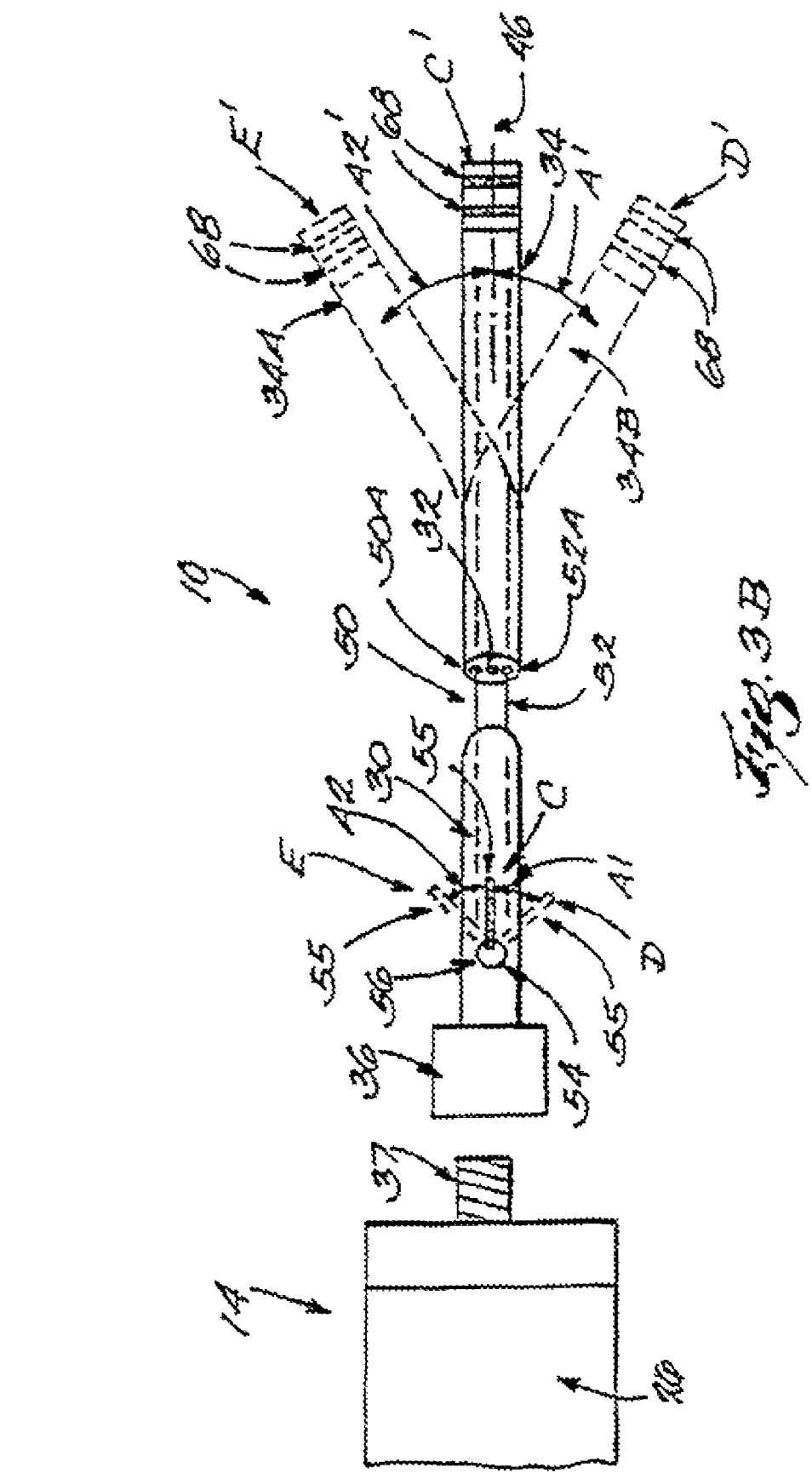
FIG. 3B is an enlarged side view of an alternative embodiment of a steerable dispensing end for the injector nozzle assembly shown in FIG. 1.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

FIG. 1 shows an injector nozzle assembly 10 for conveying a flowable material into bone. The assembly 10 is capable of carrying diverse types of flowable materials, e.g., bone cement or a suspension of one or more therapeutic substances, or both at the same time. The assembly 10 can likewise be used for diverse therapeutic purposes, as well, e.g., to treat a diseased bone, or to prevent or treat fracture or collapse of a bone, or both at the same time.

The illustrated embodiment shows the injector nozzle assembly 10 as part of a system 11, which injects cement for treating bone fracture or collapse, which is a purpose for which the assembly 10 is particularly well adapted. It should be appreciated, however, that the nozzle assembly 10 is not limited to use in the treatment of bone fractures or collapse.

FIG. 1 shows the system 11 to include a tool 12 that forms a cement-receiving cavity in cancellous bone and a tool 14, to which the assembly 10 is releasably attached to convey cement into the formed cancellous bone cavity.

In FIG. 1, the first tool 12 includes a catheter tube 16 having a distal end 18, which carries an expandable body 20. FIG. 1 shows the body 20 in a collapsed geometry, which permits the physician to insert the body 20 into the interior volume of a targeted bone. Once inserted into bone, the physician can convey fluid to expand the body 20, as shown in phantom lines in FIG. 1.

As will be described in greater detail later, expansion of the body 20 creates a cavity in cancellous bone. The use of expandable bodies to treat bones in this fashion is disclosed in U.S. Pat. Nos. 4,969,888 and 5,108,404, which are incorporated herein by reference.

The nozzle assembly 10 is deployed into the formed cavity to dispense bone cement, as will also be described in greater detail later. The cement cures and hardens to provide renewed interior structural support for cortical bone surrounding the cancellous bone.

Further details of the injection nozzle assembly 10 will now be described.

I. The Injection Nozzle Assembly

The injection nozzle assembly 10 is intended to be component that can be removably connected to a conventional injection tool 14, e.g., by a threaded connector 36 (see FIG. 2). As FIG. 1 shows, the tool 14 comprises a pistol-shaped grip, which will be referred to as a gun 22. The gun 22 includes an end fitment 24, to which a cartridge 26 is removably attached, for example, by threaded screw engagement (not shown). The cartridge 26 includes an interior, movable piston 28.

As FIG. 2 best shows, the nozzle assembly 10 comprises an injection tube 30. The injection tube is releasably coupled to the front end of the cartridge 26 by the threaded connector 36, which mates with a screw connector 37 on the cartridge.

The injection tube 30 includes a center lumen 32. The nozzle assembly 10 also includes a distal dispensing end 34, through which the center lumen 32 extends.

In use (see FIG. 1), the cartridge 26 contains bone cement 38. The cartridge 26 can be loaded with bone cement 38 in various way. For example, bone cement 38 is typically mixed in an external mixing device (not shown) from two components. Upon mixing, the two components begin to cure from a low viscosity, relatively free flowing liquid, like a thin pancake batter, to a substantially less flowable, putty like character. Eventually the cement 38 hardens to a rigid state within the targeted bone cavity formed by the expandable body 20.

Because of the increasing viscosity (lessening flow) of the bone cement 38, it should preferably be injected within a few minutes following mixing. For this purpose, a ram rod 40 extends within the gun 22. The rod 40 carries a ram disk 44. The rod 40 is coupled to a finger trigger 42.

When the physician pulls the trigger 42 rearward (as arrow 43 shows in FIG. 1), the rod 40 advances the ram disk 44 into contact with the cartridge piston 28. Advancement of the cartridge piston 28, in turn, pushes the bone cement 38 through the screw connector 37 into the lumen 32 of the injection tube 30 and out through the dispensing end 34, as FIG. 1 shows.

Details of the gun 22 can be conventional and are not essential to the invention. The gun 22 can comprise a cement gun made, for example, by Stryker Corporation (Kalamazoo, Mich.). This particular gun has a manually operated trigger with a mechanical advantage of about 9 to 1. Other injection guns may be used, having more or less mechanical advantage. Non-manually operated injection guns can also be used.

The nozzle assembly 10 can be constructed in various ways. For example, the injector tube 30, including its dispensing end 34, can be made of a plastic material, such as polyethylene or other suitable polymer. The diameter and length of the nozzle assembly 10 will vary according to the nature of the procedure. For example, for delivering cement in the hip region, the nozzle assembly 10 can be about 10 to 30 cm long with an outer diameter of about 4 to 12 mm. For delivering cement to a vertebral body, the nozzle assembly 10 can be about 18 to 30 cm long with an outer diameter of about 3 to 8 mm in diameter.

A. Deflecting the Dispensing End

As FIGS. 1 and 2 show, the dispensing end 34 of the nozzle assembly 10 is either deflected or is otherwise capable of being deflected outside the main axis 46 of the tube 30. The deflection defines radius of curvature, which aids in the deployment of the dispensing end 34 within the targeted region. The advantages of the deflected dispensing end 34 will be discussed in greater detail later, as illustrated in the context of its deployment in a vertebral body.

The deflection of the distal tube end 36 can be accomplished in various ways, which the following description exemplifies.

i. Fixed Deflection

In the embodiment shown in FIG. 2, the dispensing end 34 is normally biased into a prescribed deflected condition. The bias can be thermally set, using, for example, polyurethane or nylon material for the tube. Alternatively (as FIG. 2 shows), the dispensing end 34 can carry a length of prebent memory wire material 48, made from, e.g., a nickel-titanium alloy, which biases the dispensing end 34 toward the desired deflected geometry. The angle of the deflection can vary, according to the geometry at the intended treatment site.

As will be described in greater detail later, the bias is overcome by passage of the dispensing end 34 through a guide sheath, which temporarily straightens the dispensing end 34 during its deployment in the intended treatment site. When free of the confines of the guide sheath, the bias returns the dispensing end 34 to its preestablished deflected condition.

ii. Adjustable Deflection

In an alternative embodiment, as FIG. 3A shows, the injection tube 30 carries steering wires 50 and 52. The steering wires 50 and 52 extend through side lumens, respectively 50A and 52A in the tube 30 and are coupled to the dispensing end 34.

In FIG. 3A, two steering wires 50 and 52 are shown for the purpose of illustration, but it should be realized that more or fewer steering wires may be used. The steering wires 50 and 52 are coupled to a steering mechanism 54 located on the proximal end of the tube 30 near the gun cartridge 26, for manipulation by the physician. In FIG. 3A, the steering mechanism 54 comprises a rotatable wheel 56 with a control lever 55, to which the steering wires 50 and 52 are coupled. Other types of steering mechanisms 54, such as pull tabs or linear actuators, can be used.

Counterclockwise rotation of the wheel 56 (arrow direction A) pulls on the first steering wire 50, deflecting the dispensing end 34 upward (phantom line position 34A in FIG. 3A). Clockwise rotation of the wheel 56 (arrow direction B) pulls on the second steering wire 52, deflecting the dispensing end 34 downward (phantom line position 34B in FIG. 3A). Multi-directional steering is thereby achieved.

In an alternative embodiment (see FIG. 3B), position of the control lever 55 corresponds with the angular orientation of the dispensing end 34. When the control lever 55 is located in the center position C, the dispensing end 34 is in a straightened condition C'. When the control lever 55 is moved down or clockwise (for example, to phantom line position D) the dispensing end 34 is likewise moved to phantom line position D', and the rotation angle A1 between position C and D generally corresponds with the deflection angle A1' between position C' and D'. Likewise, when the control lever 55 is moved up or counterclockwise (for example, to phantom line position E) the dispensing end 34 is likewise moved to phantom line position E', and the rotation angle A2 between position C and E generally corresponds with the deflection angle A2' between position C' and E'.

B. Cutting the Expelled Cement Bolus i. Cutting Wires

Figure 4:
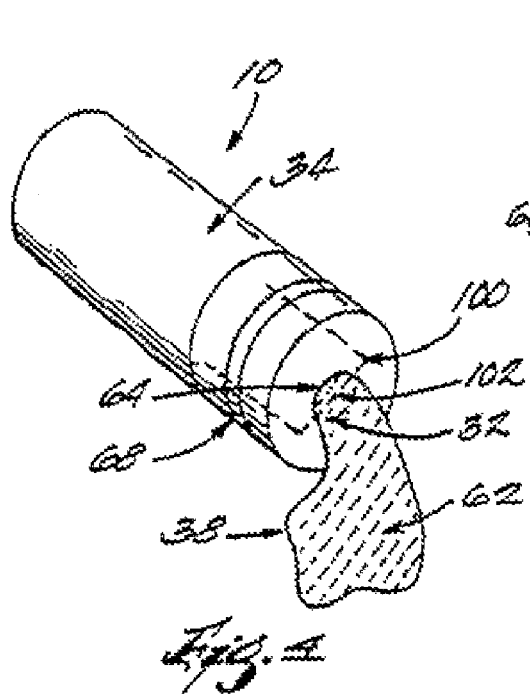
FIG. 4 is an enlarged end view of the dispensing end of one embodiment of the injector nozzle assembly shown in FIG. 1, which carries a loop formed for cutting cement free from the dispensing end.

As FIG. 4 shows, one embodiment of the nozzle assembly 10 includes a length of wire 100 carried by the dispensing end 34. The wire 100 extends across the central opening 32, forming a loop 102 for cutting loose the cement bolus 62 expelled through the lumen 32.

Figure 5:
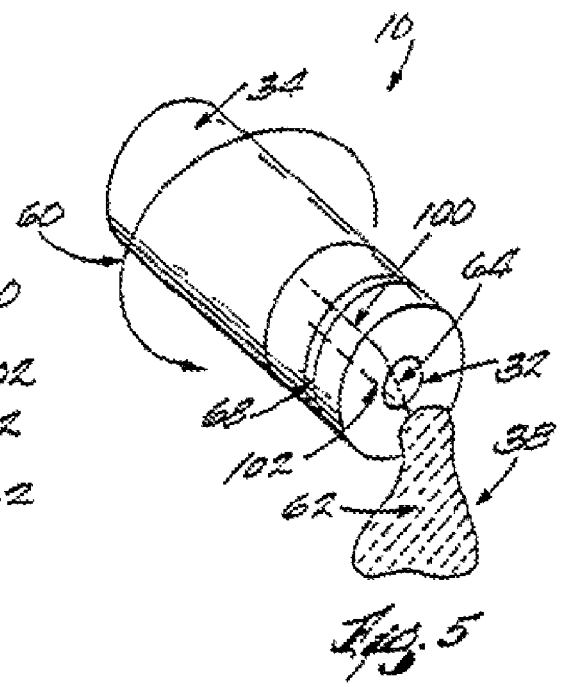
FIG. 5 is an enlarged end view of the dispensing end shown in FIG. 4, illustrating the rotation of the cement cutting loop to cut free an ejected cement bolus.

As FIGS. 4 and 5 show, rotation of the injection tube 30 (as arrow 60 in FIG. 5 shows) rotates the dispensing end 34 and, with it, the loop 102. The loop 102 rotates within the expelled bolus 62 of cement adjacent the terminal end of the lumen 32. Rotation of the loop 102 through 180.degree. cuts loose the expelled cement bolus 62 from the unexpelled cement mass 64, which resides within the dispensing end 34. The loop 102, integrally carried by the dispensing end 34, creates a consistent and clean break between the expelled bolus 62 and the unexpelled mass 64.

Figure 6:
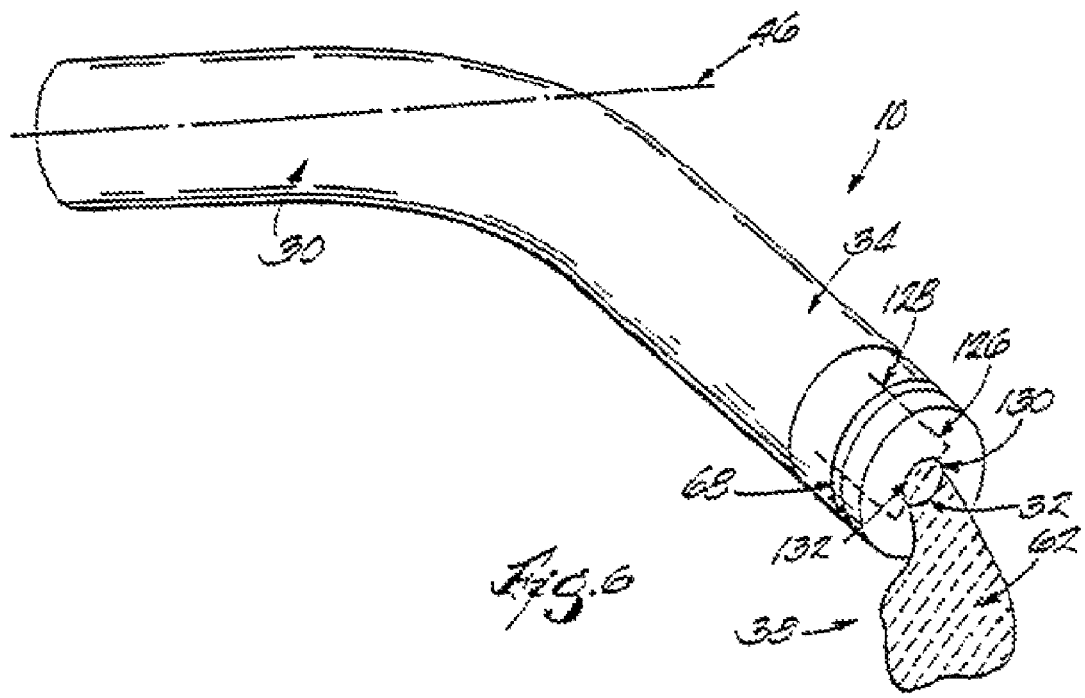
FIG. 6 is an enlarged end view of the dispensing end of one embodiment of the injector nozzle assembly shown in FIG. 1, which carries two criss-crossing loops formed for cutting cement free from the dispensing end.
Figure 5:
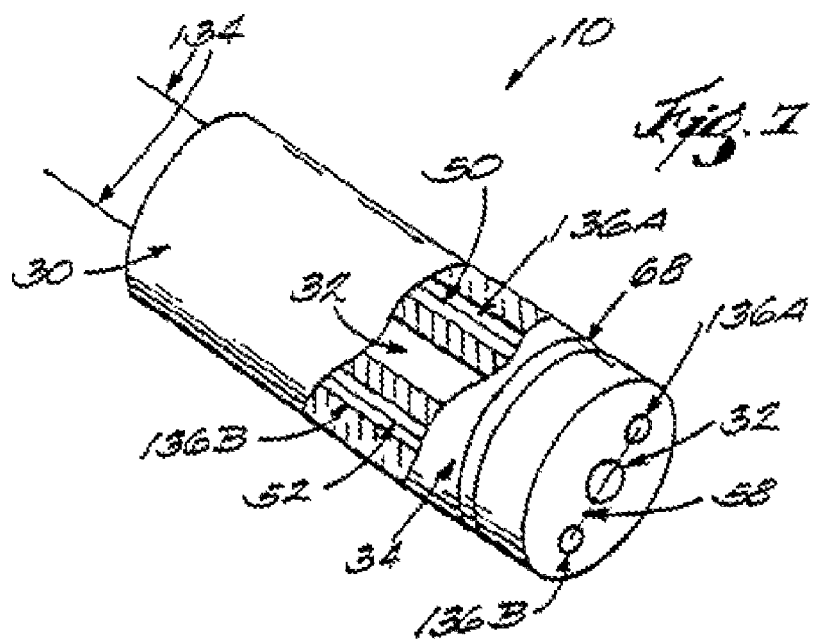
Figure 6:
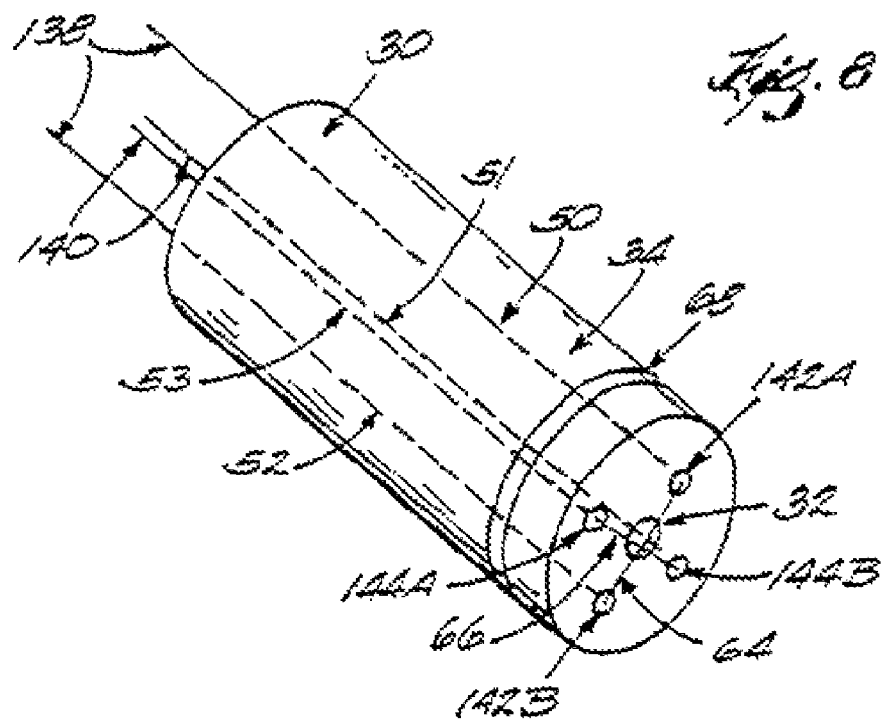

In the embodiment shown in FIG. 6, the nozzle assembly 10 includes two lengths of wire 126 and 128 carried by the dispensing end 34. The wires 126 and 128 cross over the center lumen 32, forming two cement cutting loops 130 and 132 in the path of cement expelled by the lumen 32. Rotation of the dispensing end 34 through 90.degree. passes the two loops 64 and 66 through the cement bolus 62, severing the cement bolus 62 from the cement mass residing in the dispensing end 34, in the manner shown in FIG. 5.

As FIG. 6 shows, the dispensing end 34 of the injection tube 30 shown in FIGS. 4 to 6 can, if desired, be preformed with a normal deflection, as previously described, to offset the dispensing end 34 with respect to the axis 46 of the injection tube 30. The tube 30 can also carry steering wires 50 and 52, as shown in FIG. 3, to steer the dispensing end 34.

Alternatively, the steering and cement cutting elements can be combined. For example, in the embodiment shown in FIG. 7, the nozzle assembly 10 includes a length of wire 134, which is threaded through side lumens 136A and 136B, which extend through the tube 30 (in the manner shown in FIG. 3). The wire 134 forms an exterior loop 58 at the tip of the dispensing end 34. In the illustrated and preferred embodiment, the side lumens 136A and 136B are generally diametrically spaced with respect to the center lumen 32, so that the exterior loop 58 extends across the center lumen 32, generally bisecting it. The exterior loop 58 serves as a cement cutting tool, as previously described.

In FIG. 7, the wire 134 is fixed to the tip of the dispensing end 34, so that pulling on either leg of the wire 134 will bend the dispensing end 134. The legs of the threaded wire 134 thereby serve as the first and second steering wires 50 and 52, which deflect the dispensing end 34 in the manner previously described and shown in FIG. 3.

FIG. 8 shows another alternative embodiment, in which two lengths of wires 138 and 140 are threaded through multiple pairs of side lumens 142A, 142B, 144A, and 144B, which extend through the tube 30. The wires 138 and 140 forming circumferentially spaced, multiple steering wires 50, 51, 52, and 53. The wires 138 and 140 also cross over the center lumen 32, forming two loops 64 and 66 across the dispensing end 34. The wires 138 and 140 are fixed by adhesive or other suitable manner to the tip of the dispensing end, forming multiple steering wire legs 50, 51, 52, 53. The fixed legs 50, 51, 52, and 53 provide multi-planar steering. The two loops 64 and 66 also serve as cement cutters.

FIGS. 9 to 11 show an alternative embodiment of a nozzle assembly 10, which includes a bent stylet 200 to cut loose an expelled cement bolus 62. The stylet 200 is slidably carried by an interior lumen 202 in the injection tube 30. As FIG. 11 best shows, a locating tab 206 on the stylet 200 mates with a groove or keyway 208 in the lumen 202, to prevent rotation of the stylet 200 in the lumen 202. A suitable push-pull mechanism (not shown) is accessible at the proximal end of the injection tube 30 to affect advancement and retraction of the stylet 200 in the lumen 202.

As FIG. 10 shows, the distal end 204 of the stylet 200 is preformed with an angle bend. When located in the lumen 202 (as FIG. 9 shows), the distal end 204 is retained in a straightened condition. When advanced free of the lumen 202, the distal end 204 assumes the preformed, bent configuration. The locating tab 206 and mating keyway 208 orient the stylet 200, so that, when moved free of the lumen 202, the distal end 204 bends toward and over the central opening 32 of the tube 32, as FIG. 10 shows. The distal end 204 preferably extends at least half way or more across the central opening 32 of the tube 30.

In use, while the distal stylet end 204 is withdrawn in the lumen 202, the cement bolus 62 is expressed from the central opening 32 of the dispensing end 34 (as FIG. 9 shows). When cement injection is completed, the physician slides the distal stylet end 204 forward from the lumen 202. The stylet end 204, freed from the lumen 202, bends over the central opening 32 into the cement bolus 62. Rotation of the dispensing end 34 through 360.degree. (arrow 209 in FIG. 10) passes the distal stylet end 204 through the cement bolus 62, severing the bolus 62 from the cement mass in the dispensing end 34. The physician pulls on the stylet 200 to return the distal stylet end 204 to the lumen 202.

ii. Side Injection Port

Figure 13:
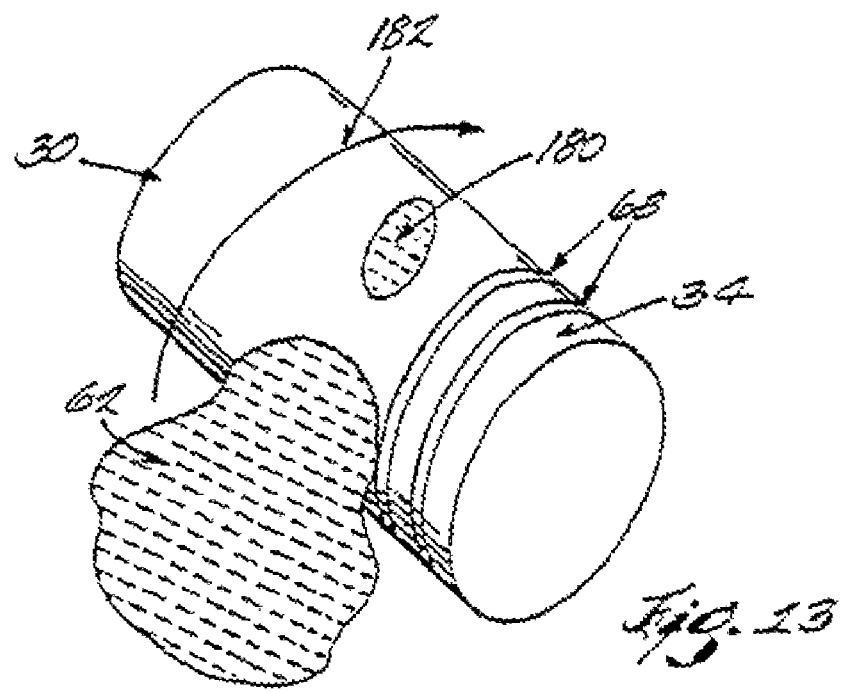
FIG. 13 is an enlarged end view of the injector nozzle assembly shown in FIG. 12, illustrating the rotation of the dispensing end to cut free an ejected cement bolus from the side dispensing port.

FIGS. 12 and 13 show another alternative embodiment of a nozzle assembly 10 which, upon rotation, cuts loose an expelled cement bolus 62.

In this embodiment, the nozzle assembly 10 includes an injection tube 30 like that shown in FIG. 2. The tube 30 includes a threaded connector 36, which screws onto the connector 37 of the cement gun cartridge 26. The tube 30 includes a center lumen 32 to transport cement from the cartridge 26 to a distal dispensing end 34.

Unlike the embodiment shown in FIG. 2, the center lumen 32 does not extend axially through the tip of the distal dispensing end 34. Instead, in FIGS. 12 and 13, the tip of the dispensing end 34 is closed and includes at least one dispensing port 180 extending at an angle from the central lumen 32. The port 180 opens on a side of the dispensing end 34.

As FIG. 13 shows, the cement bolus 62 is expressed through the side dispensing port 180, and not through the distal tip of the dispensing end 34. As FIG. 13 shows, rotation of the dispensing end 34 (indicated by arrow 182) moves the dispensing port 180 along an arc transversely of and away from the cement bolus 62. The transverse movement of the side dispensing port 180 away from the bolus 32 severs the bolus 32 from the cement mass residing in the center lumen 32.

As FIG. 12 shows, the dispensing end 34 of the injection tube 30 can, if desired, be preformed with a normal deflection, as previously described, to offset the dispensing end 34 with respect to the axis 46 of the injection tube 30. The tube 30 can also carry steering wires 50 and 52, as shown in FIG. 3, to steer the dispensing end 34.

iii. Rotating Fitting

As FIG. 14 shows, the threaded connector 36, which releasably couples the injection tube 30 to the screw connector 37 on the front end of the cartridge 26 of the cement gun 22, can include a fitting 104 that permits rotation of the injection tube 30 relative to the connector 36 and the gun 22.

Various constructions for the rotating fitting 104 are possible. In the illustrated embodiment, the rotating fitting 104 includes an adaptor 108 carried for rotation within the connector 36. The proximal end 110 of the injector tube 30 is secured to the adaptor 108 for common rotation. A retaining ring 112 outside the connector 36 surrounds tube 30, allowing its rotation but otherwise restraining rearward axial movement. An o-ring 114 is contained between the adaptor 108 and the end wall of the connector 36. The o-ring 114 restrains forward axial movement of the tube 30, while also preventing leakage of cement.

The rotating fitting 104 permits the physician to rotate the injection tube 30 with one hand, and thereby rotate the nozzle 34 (as arrows 106 show in FIG. 14), while holding the gun 22 stationary in another hand. As FIG. 14 shows, the injection tube 30 can carry a hub or grip 115 to facilitate rotation.

The rotating fitting 104 simplifies handling and manipulation of the cement injection tool 14 during rotation of the injection tube 30. The physician is able to rotate the injection tube 30, causing the one or more cement cutting loops carried by the rotating dispensing end 34 to cut loose an expelled cement bolus 62 (as shown in FIGS. 4 and 5, 9 and 10, and 12 and 13), without rotating the gun 22 itself. When combined with a deflected dispensing end 34, rotation of the tube 30 further helps locate the dispensing end 34 in the desired position, again without the need to rotate the gun 22.

As FIG. 15 shows, the rotating fitting 104 can include indicia to gauge orientation or rotation of the injection tube 30. In the illustrated embodiment, the indicia includes an index mark 210 scribed on the connector 36, which aligns with an index mark 212 scribed on the proximal end of the injection tube 30. Alignment of the marks 210 and 212 places the dispensing end 34 in a particular, preestablished orientation.

For example, when the dispensing end 34 is normally biased in a deflected condition, as FIG. 15 shows, alignment of the marks 210 and 212 can designate that the deflection is to the right of the main axis 46. The index mark 210 can also include a visual or tactile identifier (for example, a raised letter "R" in FIG. 15) to further aid the physician in ascertaining the orientation.

The fitting 104 can also include additional auxiliary index marks (two of which 214 and 216 are shown in FIG. 15) and associated visual or tactile identifiers (respectively, "U" and "D"). Alignment of the mark 212 with auxiliary mark 214 indicates that the deflection orients the dispensing end 34 upward. Likewise, alignment of the mark 212 with auxiliary mark 216 indicates that the deflection orients the dispensing end 34 downward. Another auxiliary mark and associated identifier (not shown), located diametrically opposite to the mark 210, can also indicate a left orientation of the deflected dispensing end 34.

The alignment of the index mark 212 with the index marks 210, 214, and 216 allows the physician to remotely orient the deflected end 34 in a desired way, without reliance upon x-ray or other internal visualization technique. Tracking the rotation of the index mark 212 relative to one or more of the index marks 210, 214, or 216 also allows the physician to gauge the rotation of the injection tube 30, to achieve the degree of rotation necessary to cut the cement bolus 62 loose.

When the dispensing end 34 is steerable (as shown in FIG. 3), alignment of the marks 210 and 212 can designate that the steering wires 50 and 52 extend in a particular vertical or horizontal plane. With this orientation known, the physician can operate the steering mechanism 56 to achieve the desired bending action, without reliance upon x-ray or other form of internal visualization. Relative movement of the index marks also allows the physician to monitor the extent of rotation of the injection tube 30 when cutting the cement bolus 62 loose.

When the dispensing end 34 includes a side dispensing port 180 (as shown in FIGS. 12 and 13), alignment of the marks 210 and 212 can designate the orientation of the dispensing port 180, either left, right, up, or down. Relative movement of the index marks also allows the physician to monitor the extent of rotation of the injection tube 30 when cutting the cement bolus 62 loose.

C. Radiological Monitoring

In all the embodiments shown in FIGS. 2 to 15, the nozzle assembly 10 includes one or more radiological markers 68. The markers 68 are made from known radiopaque materials, like platinum, gold, calcium, tantalum, and other heavy metals. At least one marker 68 is placed at or near the dispensing end 34, to allow radiologic visualization of the dispensing end 34 within the targeted bone area.

Other forms of markers can be used to allow the physician to visualize the location of the dispensing end 34 within the targeted treatment area.

II. Deployment of Nozzle Assembly in a Vertebral Body

Figure 16:
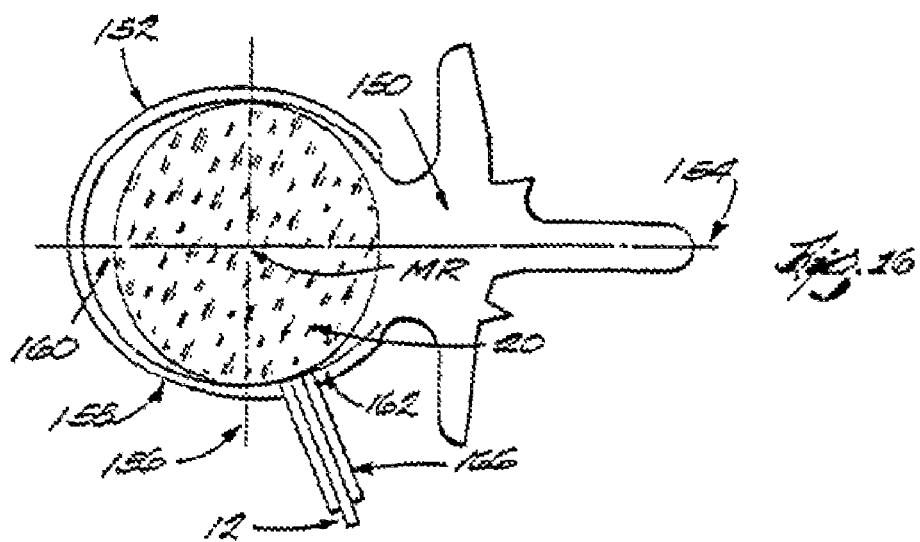
FIG. 16 is a coronal view of a vertebral body, partially cut away and in section, illustrating the deployment, by postero-lateral access, of an expandable body to compress cancellous bone and form an interior cavity.

Use of the nozzle assembly 10 will now be described when deployed in a human vertebra 150, which FIG. 16 shows in coronal (top) view. It should be appreciated, however, the nozzle assembly 10 is not limited in its application to vertebrae. The system 10 can be deployed equally as well in long bones and other bone types.

The vertebra 150 includes a vertebral body 152, which extends on the anterior (i.e., front or chest) side of the vertebra 150. The vertebral body 152 includes an exterior formed from compact cortical bone 158. The cortical bone 158 encloses an interior volume of reticulated cancellous, or spongy, bone 160 (also called medullary bone or trabecular bone).

The vertebral body 152 is in the shape of an oval disk, which is generally symmetric about an anterior-posterior axis 154 and a mid-lateral axis 156. The axes 154 and 156 intersect in the middle region or geometric center of the body 152, which is designated MR in the drawings.

As FIG. 16 shows, access to the interior volume of the vertebral body 152 can be achieved. e.g., by drilling an access portal 162 through a side of the vertebral body 152, which is called a postero-lateral approach. The portal 162 for the postero-lateral approach enters at a posterior side of the body 152 and extends at angle forwardly toward the anterior of the body 152. The portal 162 can be performed either with a closed, minimally invasive procedure or with an open procedure.

As FIG. 16 shows, a guide sheath 166 is located in the access portal 162. Under radiologic, CT, or MRI monitoring, the tool 12 is introduced through the guide sheath 166, with the expandable body 20 collapsed. When deployed in the cancellous bone 160, the physician conveys a pressurized fluid into the body 20 to expand it. The fluid is preferably radio-opaque to facilitate visualization. For example, Renografin™ contract media can be used for this purpose.

Expansion of the body 20 within the interior volume compresses cancellous bone 160 to form a cavity 164. The compaction of cancellous bone also exerts interior force upon cortical bone 158, making it possible to elevate or push broken and compressed bone back to or near its original prefracture position.

The body 20 is preferably left inflated for an appropriate waiting period, for example, three to five minutes, to allow coagulation inside the vertebral body 152. After the appropriate waiting period, the physician collapses the body 20 and removes it. As FIG. 17 shows, the formed cavity 164 remains in the interior volume of the vertebral body 152.

Figure 17:
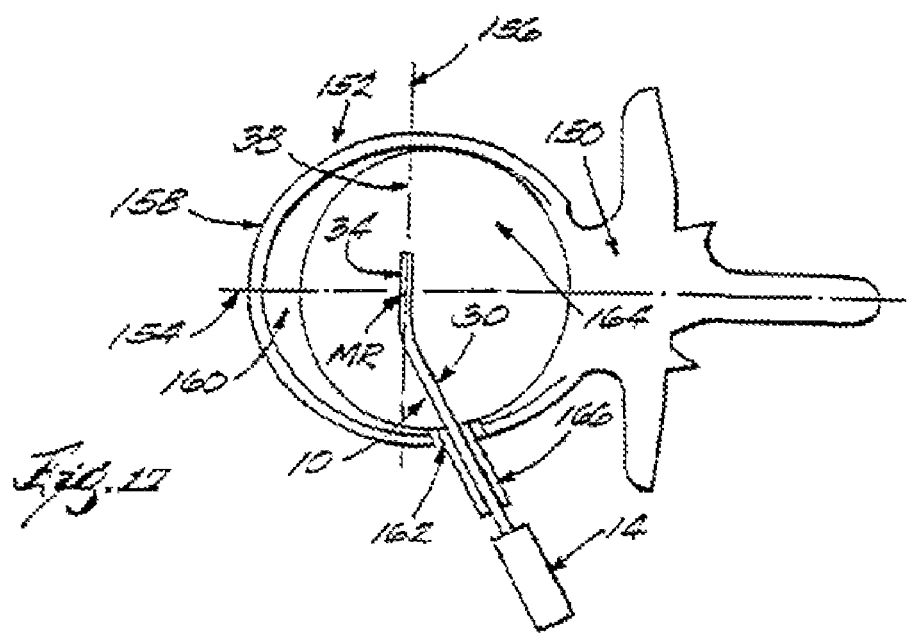
FIG. 17 is a coronal view of the vertebral body shown in FIG. 16, illustrating the deployment of the injector nozzle assembly shown in FIG. 1 by postero-lateral access.

As FIG. 17 shows, the second tool 14 is now readied for deployment. With the cartridge 26 filled with cement 38, the physician directs the injection tube 30 through the guide sheath 166 into the formed cavity 164.

If the dispensing end 34 is normally biased into a bent condition (as exemplified in FIG. 2), passage through the guide sheath 166 overcomes the bias and straightens out the dispensing end 34. Once free of the guide sheath 166, the dispensing end 34 returns to its normally biased condition.

Figure 19A:
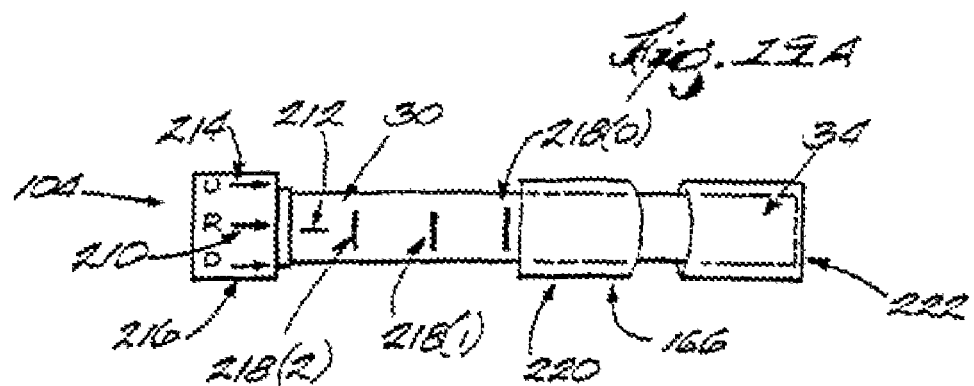
FIGS. 19A, 19B, and 19C are side views of an injector nozzle assembly, which also includes index markers for ascertaining the extent to which the dispensing end is extended into the targeted treatment site, without the need for direct visualization.
Figure 19B:
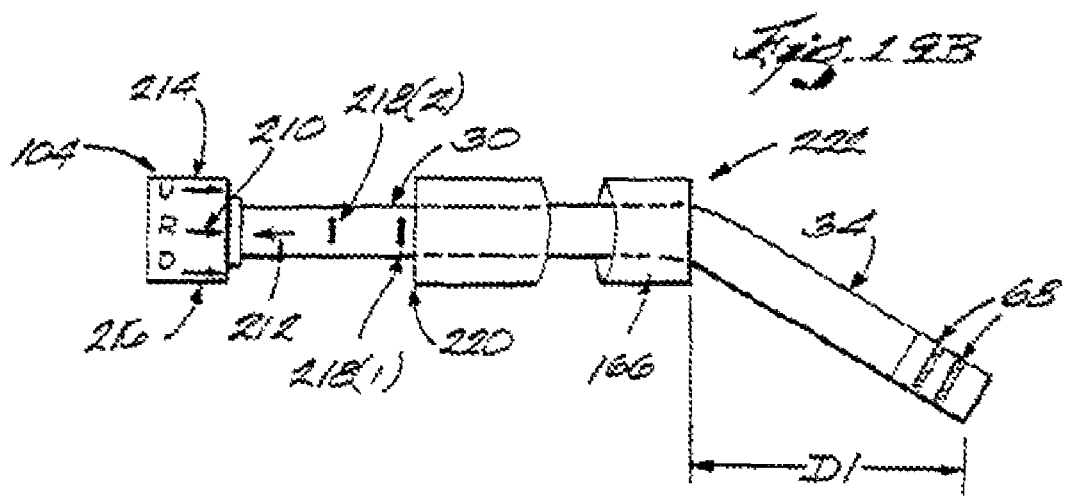
Figure 19C:
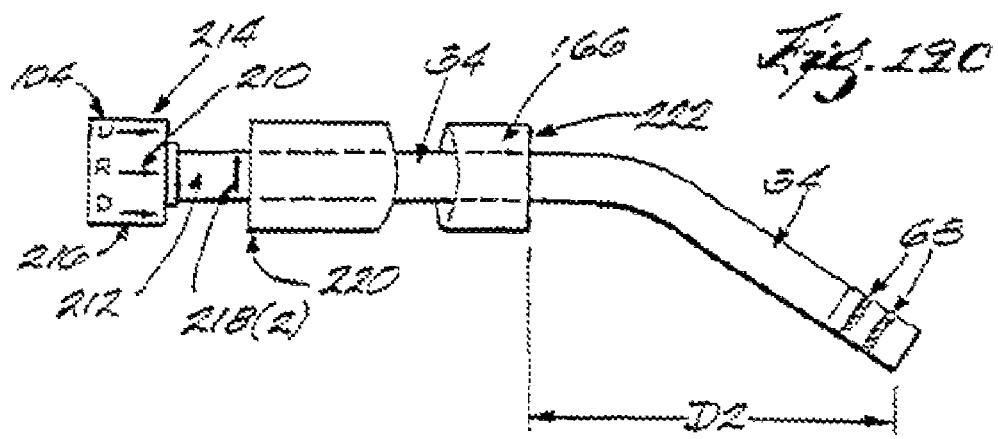

As shown in FIGS. 19A, 19B, and 19C, the tube 30 can include prepositioned markers 218(0) to 218 (2) along its length. The markers 218(0) to 218(2) are positioned to successively align with the proximal edge 220 of the guide sheath 166 at intervals that mark the extent to which the dispensing end 34 extends beyond the distal edge 222 of the guide sheath 166.

As FIG. 19A shows, when marker 218(0) and the proximal edge 220 align, the distal edge 222 of the guide sheath 166 and the dispensing end 34 are coincident (i.e., the tip of the dispensing end 34 coterminous with the distal edge 222 of the sheath 166).

As FIG. 19B shows, subsequent movement of the tube 30 in the sheath 166 brings the marker 218(1) into alignment with the proximal edge 220. This alignment indicates that the tip of the dispensing end 34 projects beyond the distal edge 222 by a first, predetermined distance D1.

As FIG. 19C shows, subsequent movement of the tube 30 to further advance the dispensing end 34 brings the marker 218(2) into alignment with the proximal edge 220. This alignment indicates that the dispensing end 34 projects beyond the distal edge 222 by a second, predetermined distance D2.

Of course, the number and spacing of the markers 218 can vary. The markers 218 allow the physician to gauge when and to what extent the dispensing end 34 projects into the targeted site, without need for direct visualization.

Under radiologic visualization provided by the markers 68, the physician may rotate the injection tube 30. Rotation of the injection tube 30 orients the dispensing end 34 within the cavity 164 before or during the injection of cement 38. In the embodiment shown in FIG. 14, the rotation may be accomplished without rotating the gun 22. In the embodiment shown in FIG. 15, the extent of rotation and the orientation of the dispensing end 34 can be observed using the markers 212/210, 214, and 216 on the fitting 104 (see FIG. 15), without active internal visualization.

Alternatively, if the tube 30 carries one or more steering wires 50 and 52 (as exemplified in FIG. 3), the physician may selectively bend the dispensing end 34 under radiological visualization provided by the markers 68. In this way, the physician can steer the dispensing end 34 into the desired position or positions within the cavity 164 before or during injection of cement 38. In the embodiment shown in FIG. 15, the markers 212/210, 214, and 216 on the fitting 104 aid the steering process (see FIG. 15), without active internal visualization.

As shown in FIG. 17, the postero-lateral access portal 162 does not align the injection tube 30 with the geometric axes 154 and 156 of the vertebral body 152. Nevertheless, deflection of the dispensing end 34 aligns the end 34 in the middle region MR of the body 152 along the mid-lateral axis 156.

As FIG. 17 shows, the gun 22 urges the cement 38, or other filling material, into the cavity 164. While injecting the material 38, the physician preferably begins with the dispensing end 34 positioned in the lateral region opposite to the access portal 162. As the material 38 flows into the cavity 164, the physician progressively moves the dispensing end 34 along the mid-lateral axis 156 through the middle region MR and toward the access portal 162. The deflection of the dispensing end 34 (by virtue of either the preformed bias or by active steering) allows the physician to maintain the desired alignment with the mid-lateral axis 156. The deflection of the dispensing end 34 (by virtue of either the preformed bias or by active steering) also allows the physician to keep the dispensing end 34 continuously submerged in the filling material 38, to thereby avoid the formation of air or fluid pockets.

The physician observes the progress of the injection radiologically using the markers 68, positioning the dispensing end 34 by rotation or steering, or both, as just described.

The physician flows material 38 into the cavity 164, until the material 38 reaches the interior end of the guide sheath 166. If the dispensing end 34 carries one or more exterior loops (as exemplified in FIGS. 4 to 10), or a side dispensing port 180 (as exemplified in FIGS. 12 and 13), rotation of the dispensing end 34 will cleanly sever the injected cement bolus residing in the cavity 164 from the unexpelled cement residing within the dispensing end 34 (as FIGS. 4 and 5 and FIGS. 12 and 13 show). In this way, cement residing in the cavity 164 will not be inadvertently drawn out of the cavity 164 upon withdrawal of the dispensing end 34. Rotation of the dispensing end 34 to sever the material bolus also avoids the formation of sharp pedicles in the material bolus, which could irritate surrounding tissue.

In the embodiment shown in FIG. 15, the markers 212/210, 214, and 216 on the fitting 104 aid in monitoring the extent of rotation, without active internal visualization.

As FIG. 18 shows in a lateral view, access into the interior volume of a vertebral body 152 can also be accomplished by drilling an access portal 168 through either pedicle 170. This is called a transpedicular approach. As FIG. 18 shows, the access portal 170 for a transpedicular approach enters at the top of the vertebral body 152, where the pedicle 170 is relatively thin, and extends at an angle downward toward the bottom of the vertebral body 152 to enter the interior volume.

The tool 12 is deployed through a guide sheath 166 in the portal 168 to form a cavity 172, in the same manner described above. The physician can manipulate the second tool 14 to steer the dispensing end 34 of the nozzle assembly 10 into the cavity 172. Although the transpedicular access portal aligns the tube 30 obliquely with respect to the axes 154 and 156, the deflected dispensing end 34 can be rotated into general alignment with either the anterior-posterior axis 154 or the mid-lateral axis 156 while injecting cement.

The deflected dispensing end 34 allows the introduction of cement 38 into the middle region MR of the vertebral body 152, using either postero-lateral access or a transpedicular access. The cement 28, when hardened, provides support uniformly across the middle region MR. The capability of the vertebral body 152 to withstand loads is thereby enhanced.

The above described procedure, carried out in a minimally invasive manner, can also be carried out using an open surgical procedure. Using open surgery, the physician can approach the bone to be treated as if the procedure is percutaneous, except that there is no skin and other tissues between the surgeon and the bone being treated. This keeps the cortical bone as intact as possible, and can provide more freedom in accessing the interior volume of the vertebral body 152.

III. Cooled Nozzle Assembly

After mixing and while curing, the cement 38 undergoes a chemical reaction that generates heat. When the cement temperature is below a given threshold value, the cement 38 maintains a flowing, viscous liquid state, which is suited for introduction through the nozzle assembly 10 into the targeted region. As the temperature increases beyond the threshold value, the cement 38 begins to harden, progressively losing its flow characteristic and becoming more resistant to passage through the nozzle assembly 10. It is desirable to expel the loose cement bolus 62 before the threshold temperature is reached.

FIG. 20 shows a system 240 for cooling the nozzle assembly 10 during passage of the cement 38 through the dispensing end 34. The system 240 includes the injection tube 30, which is releasably coupled to the front end of the cartridge 26 by the threaded connector 36, as previously described. The tube 30 includes the center lumen 30, through which cement 38 conveyed from the cartridge 26 passes.

Figure 22:
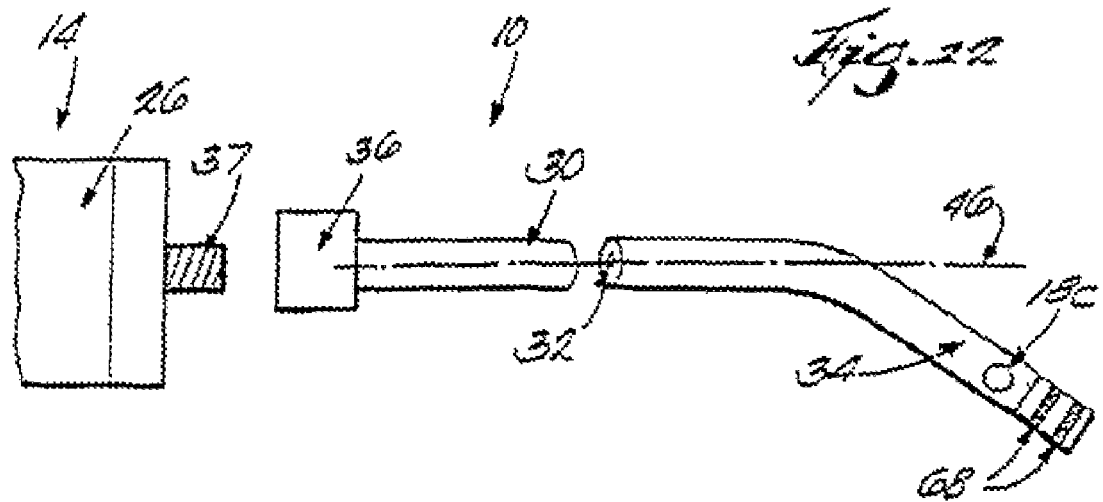
FIG. 22 is an end view of the injector nozzle assembly shown in FIG. 20.

The system 240 further includes at least one paired set of side lumens, which extend through the tube 30 axially beside the center lumen 30. In the illustrated embodiment (see FIG. 22), four paired lumen sets are shown, designated 242 A and B, 244 A and B, 246 A and B, and 248 A and B. As shown in FIGS. 21 and 22, each lumen set 242A/B; 244A/B; 246A/B; and 248A/B comprises a closed loop for carrying a cooling fluid from a source 250, through the tube 30, and to waste 252.

As best shown in FIG. 21, the lumen designated A in each set 242A/B; 244A/B; 246A/B; and 248A/B communicates at its proximal end with the cooling fluid source 250 via an in line pump 254. The lumen designated A in each set 242A/B; 244A/B; 246A/B; and 248A/B therefore comprises an inlet path for the cooling fluid.

As FIG. 21 also shows, the inlet lumen A of each set 242A/B; 244A/B; 246A/B; and 248A/B communicates at its distal end with the distal end of the lumen designated B in its respective set 242A/B; 244A/B; 246A/B; or 248A/B. As FIGS. 21 and 22 show, communication between the distal ends of the lumens A and B in each set 242A/B; 244A/B; 246A/B; and 248A/B is established by removing material between the lumens A and B to form a channel 256 between them, and laying a sealing material 258 over the channel 256. The proximal ends of the lumens B in each set 242A/B; 244A/B; 246A/B; and 248A/B communicate with waste 252. The lumen B of each set 242A/B; 244A/B; 246A/B; and 248A/B thereby comprises a return path for the cooling fluid.

At the source 250, the cooling fluid is at a desired temperature, which is cooler than the threshold temperature of the cement 38. For example, the source fluid can comprise tap water at a temperature of about 68.degree. F. (20.degree. C.). While cement 38 is conveyed by the center lumen 32 for discharge, the pump 254 conveys cooling fluid from the source 250 through the inlet paths 242A, 244A, 246B, and 248B. The return paths 242B, 244B, 246B, and 248B carry the cooling fluid to waste 252. The circulation of cooling fluid in the tube 30 along the center lumen 32 dissipates heat generated by the curing cement 38, to mediate the temperature increase in the curing cement 38. The circulation of cooling fluid thereby keeps the curing cement 38 in the center lumen 32 in a viscous flowing condition for a longer period of time.

In the illustrated embodiment (see FIGS. 20 and 21), the return paths 242B, 244B, 246B, and 248B convey cooling fluid to waste 252 downstream of proximal end of the center lumen 30. This quickens the discharge of heated return fluid from the tube 30 to thereby further minimize the temperature increase within the center lumen 32.

It should be appreciated that the system 250 can also include a cutting element to sever the cement flow in response to rotation of the tube 30, as well as means for deflecting the dispensing end 34, in any of the manners previously described.

IV. Injector Nozzle Assembly with Variable Delivery Rates

Figure 25:
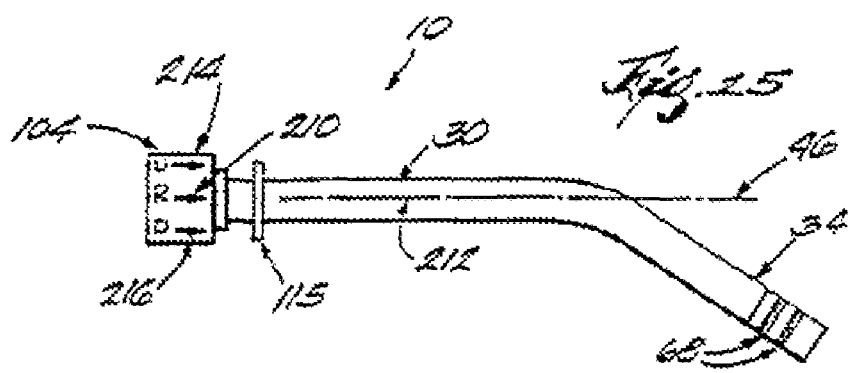
FIG. 25 is an exploded view, with portions broken away and in section, of the injector nozzle assembly shown in FIG. 23.

FIGS. 23 to 25 show another embodiment of an injector nozzle assembly 300 for conveying a flowable material 302 into bone or another location, such as a cavity, in the body. Like the injector nozzle assemblies previously described, the assembly 300 shown in FIGS. 23 to 25 is capable of carrying diverse types of flowable materials, e.g., bone cement or a suspension of one or more therapeutic substances, or both at the same time. The assembly 300 shown in FIGS. 23 and 24 can likewise be used for diverse therapeutic purposes, as well, e.g., to treat a diseased bone, or to prevent or treat fracture or collapse of a bone, or both at the same time.

Figure 26:
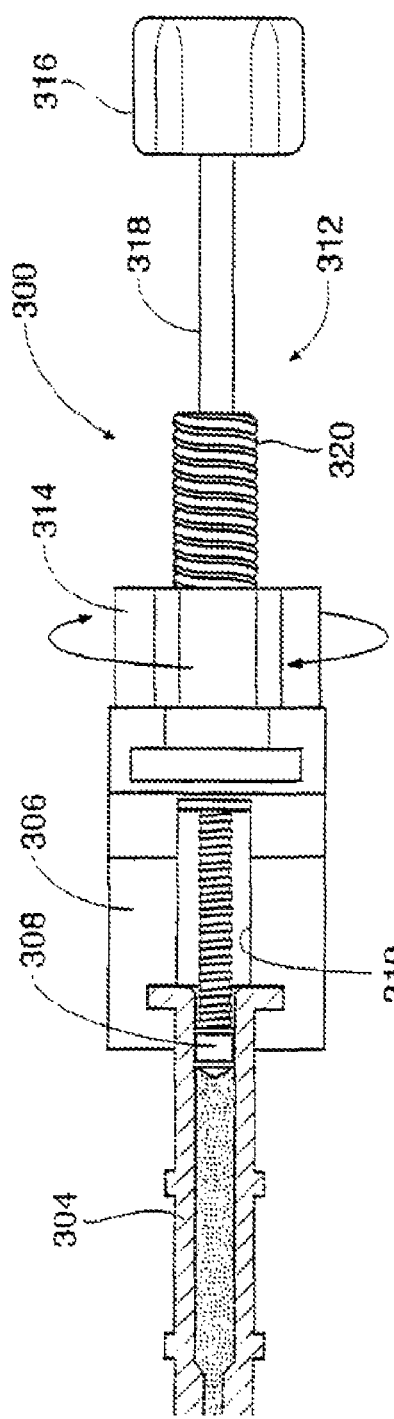
FIG. 26 is a side view, with portions broken away and in section, of the injector nozzle assembly shown in FIG. 23, being operated to provide a fast rate, high volume delivery of flowable material.
Figure 27:
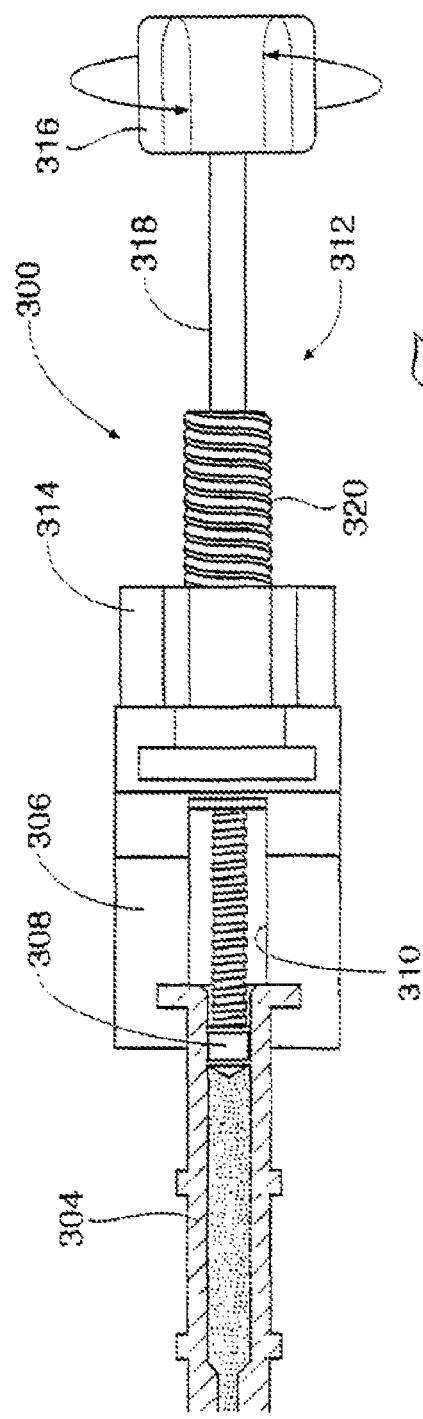
FIG. 27 is a side view, with portions broken away and in section, of the injector nozzle assembly shown in FIG. 23, being operated to provide a slower, metered delivery rate of flowable material.

As shown in FIGS. 23 to 25, the assembly 300 comprises a syringe body 304 coupled to a syringe handle 306. In use, a volume of flowable material 302 is loaded into the syringe body 304 (see FIGS. 26 and 27). As FIG. 24 best shows, a syringe plunger 308 is carried in a plunger chamber 310 formed in the interior of the syringe handle 306. The syringe plunger 308 axially advances through the syringe body 304, thereby expelling the flowable material 302 out the distal end of the syringe body 304 (as FIGS. 26 and 27 show).

The syringe handle 306 and syringe body 304 can comprise, e.g., formed plastic or metal parts. The syringe handle 306 can be formed to possess different shapes and sizes. It is desired that the handle 306 is sized to fit comfortably in the hand of an operator.

The syringe body 304 can comprise a component that can be easily coupled to the handle 306 at time of use and then decoupled from the handle 306 and discarded after use. An O-ring 334 (see FIG. 25) desirably seals the periphery of the releasable junction between the body 304 and the handle 306. Syringe bodies 304 possessing different lengths and/or different interior volumes can also be provided, to meet the particular delivery objectives of the targeted site. The syringe plunger 308 desirably comprises a material, e.g., polyisoprene rubber, that makes moving sealing engagement against the interior wall of the syringe body 304, to exert an expelling force upon the material 302.

A plunger advancement mechanism 312 is carried by the syringe handle 306, as FIGS. 23 and 24 best show. The mechanism 312 is coupled to the syringe plunger 308. As FIGS. 26 and 27 show, force applied to the plunger advancement mechanism 312 causes the syringe plunger 308 to move axially through the plunger chamber 310 and the syringe body 304, thereby expelling the flowable material from the body 304.

Desirably, the plunger advancement mechanism 312 is configured to accommodate different delivery objectives. For example, in a first delivery mode, the advancement mechanism 312 causes the syringe plunger 308 to advance or retract a set distance per rotation of a first actuator 314. In a second delivery mode, the advancement mechanism 312 causes the syringe plunger 308 to advance or retract at a different set distance per rotation of a second actuator 316.

In the illustrated embodiment, the first axial displacement is greater than the second axial displacement. The operator is thereby able to expel material 302 from the syringe body 304 in the first delivery mode more quickly per rotation of the actuator than in the second delivery mode. The operator can thereby easily switch from a relatively rapid, high volume discharge of flowable material, when so desired, to relatively slower, more metered, lower volume discharge of flowable material, when so desired. The operator is also able, in the first, high volume delivery mode, to rapidly retract the syringe plunger 308, to withdraw the pressure force of the syringe plunger 308 against the material 302, to thereby quickly terminate the flow of material from the syringe body 304. The ability to start and stop both large volume flow and metered, smaller volume flow makes it possible to rapidly respond to in situ flow conditions, to thereby prevent or minimize the flow of material 302 under pressure through cracks, openings, or voids in cortical bone, in a process called "extravazation." The operation of the plunger advancement mechanism 312 to achieve a variable rate of delivery can be implemented in various ways. In the illustrated embodiment, the plunger advancement mechanism 312 responds to the application of rotational force to advance the syringe plunger 308. In this arrangement, rotatable first and second actuators or control knobs 314 and 316 are carried at the proximal end of the syringe handle 306. In use, the operator holds the syringe handle 306 in one hand, while applying force with the other hand to rotate either the first or second control knob 314 and 316. As FIG. 26 shows, rotation of the first control knob 314 advances the syringe plunger 308 at a first axial displacement per rotation, to discharge a given volume of material 302 per amount of rotation. As FIG. 27 shows, rotation of the second control knob 316 advances the syringe plunger 308 at a slower, second axial displacement per rotation, discharging a lesser volume of material 302 per amount of rotation.

In the illustrated embodiment (see FIG. 25), the syringe plunger 308 is attached to the distal end of a threaded slow advancement screw 318. In the illustrated embodiment, a snap fit clip 332 is provided on the distal end of the slow advancement screw to couple the plunger 308 to the screw 318. The second rotatable control knob 316 is attached to the opposite end of the slow advancement screw 318, to rotate the slow advancement screw 318 about its axis.

The threaded slow advancement screw 318 is itself carried within the bore 322 of an externally threaded fast advancement screw 320. The exterior threads 324 of the slow advancement screw 318 engage interior threads 326 in the bore 322 of the fast advancement screw 320 (see FIG. 25). Rotation of the slow advancement screw 318 about its axis causes the slow advancement screw 318 to move relative to the fast advancement screw 320, either fore or aft, depending upon the direction of rotation. The syringe plunger 308 carried at the end of the screw 318 is thereby also caused to move.

The fast advancement screw 320 is itself coupled to the first control knob 314, which is rotatably coupled to the syringe handle 306. The first control handle 314 includes an annular, internally threaded aperture 328 (see FIG. 25). The threaded aperture 328 engages the external threads 330 of the fast advancement screw 320. As FIG. 23 shows, when the fast advancement screw 320 is threadably engaged in the first control knob 314, the slow advancement screw 318, which is itself threaded in the fast advancement screw 320, extends into the handle 306. The syringe plunger 308, carried at the distal end of the slow advancement screw 318, extends into the plunger chamber 310. Rotation of the first control knob 314 about the fast advancement screw 320 moves the fast advancement screw 320 fore or aft, depending upon the direction of rotation. The slow advancement screw 318 moves in tandem with the fast advancement screw 320, causing the syringe plunger 308 to also move in the plunger chamber 310 and syringe body 304 in response to rotation of the first control knob 314. As before explained, rotation of the second control knob 316 will likewise independently cause movement of the slow advancement screw 318 within the fast advancement screw 320, likewise moving the syringe plunger 308 within the plunger chamber 310 and syringe body 304. The distance and direction that the syringe plunger 308 travels in one rotation of either the slow advancement screw 318 or the fast advancement screw 320 is controlled by the configuration of the mating threads.

In a representative embodiment, the exterior threads 324 of the slow advancement screw 318 comprise 10-degree modified right handed square threads (class 2G, single start), with sixteen threads to the inch. In this arrangement (see FIG. 27), clockwise rotation of the slow advancement screw 318 advances the syringe plunger 308 toward the distal end of the syringe body 304, and counter-clockwise rotation of the slow advancement screw 318 retracts the syringe plunger 308 away from the distal end of the syringe body 304. One revolution of the second control knob 316 moves the syringe plunger 308 about one-sixteenth (1/16th) of an inch.

Likewise, in a representative embodiment, the exterior threads 326 of the fast advancement screw 320 comprise 10-degree modified left handed square threads (class 2G, three start), with six threads to the inch. In this arrangement (see FIG. 26), counter-clockwise rotation of the fast advancement screw 320 retracts the syringe plunger 308 away from the distal end of the syringe body 304, and clockwise rotation of the fast advancement screw 320 advances the syringe plunger 308 toward the distal end of the syringe body 304. One revolution of the first control knob 314 moves the syringe plunger 308 about one-half (½) inch. Thus, a single rotation of the first control knob 314 moves the syringe plunger 308 farther than a single rotation of the second control knob 316, expelling a greater volume of material 302 per rotation of the actuator.

As described, the plunger advancement mechanism 312 is operated manually. It should be appreciated that the plunger advancement mechanism can be operated by means of an electric motor or the like.

The assembly 300 shown in FIGS. 23 to 27 can be used to convey material 310 into a cavity created in cancellous bone by an expandable structure, as earlier described and as shown in FIGS. 16 and 17. The assembly 300 may also be used in association with a vertebroplasty procedure, which injects cement under pressure into a vertebral body, without prior formation of a cavity.

In a representative embodiment, the syringe handle 306 (which can be made of polycarbonate) measures about 3.9 inches in length and 2.6 inches in width. The syringe body 304 (which also can be made of polycarbonate) measures about 5.1 inches in overall length, with an interior lumen having an inside diameter of about 0.5 inch.

In this representative embodiment, the first control knob 314 (which can be made from Celcon™ plastic material) is shaped round and has a diameter of about 2.5 inches. The fast advancement screw 320 (which can also be made from Celcon™ plastic material) has a length of about 4.5 inches and an outside thread diameter of about 0.75 inch. The internal threads extend for a distance of about 0.75 inch.

In this representative embodiment, the slow advancement screw 318 (which can also be made from Celcon™ plastic material) extends from the second control knob 316 for a length of about 9.35 inches and has an outside thread diameter of about ⅜ inch. The second control knob 316 is elliptical in shape, measuring about 2.0 inches along its major axis, about 0.625 inch along its minor axis, and about 1.5 inches in height.

The features and advantages of the invention are set forth in the following claims.

What is claimed is:

1. A system comprising
a guide tool for establishing a percutaneous access path along an access axis to a vertebral body having a cortical wall enclosing a cancellous bone volume, the tool having a distal end, a proximal end, and an inner bore;
an assembly for conveying a flowable material into the vertebral body, the assembly comprising a filling material dispenser and a tube body sized for passage within the inner bore of the guide tube and including a flexible dispensing end sized and configured for placement within the vertebral body to dispense a volume of filling material in the vertebral body, the assembly further comprising a steering apparatus for deflecting the flexible dispensing end of the tube body within the vertebral body.

2. The system of claim 1 wherein the assembly further comprising a connector for connecting the filling material dispenser to the tube body, wherein the connector permits the tube body to rotate relative to the filling material dispenser.

3. The system of claim 1 wherein the steering apparatus comprises a rotatable wheel.

4. The system of claim 1 wherein the steering apparatus is operable to deflect the flexible dispensing end in multiple directions.

5. The system of claim 1 wherein the steering apparatus is operable to control an angular orientation of the flexible dispensing end relative to the access axis of the guide tool.

6. The system of claim 1 wherein the flexible dispensing end is deflectable between a straightened configuration for passage through the inner bore of the guide tool and a deflected configuration when located beyond the distal end of the guide tool for dispensing the volume of filling material into the vertebral body.

7. The system of claim 1 wherein the steering apparatus comprises at least one steering wire.

\* \* \* \* \*